(12) United States Patent
Damian et al.

(10) Patent No.: US 8,206,986 B2
(45) Date of Patent: Jun. 26, 2012

(54) METHODS FOR DETECTING ALZHEIMER'S DISEASE

(75) Inventors: Doris Damian, West Newton, MA (US); Amir Handzel, Rahway, NJ (US); Aram Adourian, Woburn, MA (US)

(73) Assignee: BG Medicine, Inc., Waltham, MA (US)

( * ) Notice: Subject to any disclaimer, the term of this patent is extended or adjusted under 35 U.S.C. 154(b) by 103 days.

(21) Appl. No.: 11/918,078

(22) PCT Filed: Mar. 13, 2006

(86) PCT No.: PCT/US2006/009042
§ 371 (c)(1),
(2), (4) Date: Feb. 4, 2009

(87) PCT Pub. No.: WO2006/099377
PCT Pub. Date: Sep. 21, 2006

(65) Prior Publication Data
US 2009/0211346 A1    Aug. 27, 2009

Related U.S. Application Data

(60) Provisional application No. 60/661,393, filed on Mar. 14, 2005.

(51) Int. Cl.
*G01N 30/68* (2006.01)
*G01N 30/00* (2006.01)

(52) U.S. Cl. ....... 436/63; 73/61.55; 73/61.52; 73/61.43; 73/61.41; 73/53.01

(58) Field of Classification Search ............... 436/63; 73/61.55, 61.52, 61.43, 61.41, 53.01
See application file for complete search history.

(56) References Cited

U.S. PATENT DOCUMENTS
5,617,861 A    4/1997    Ross et al.

FOREIGN PATENT DOCUMENTS
WO    2004/030522 A2    4/2004
WO    2005/001483 A2    1/2005

OTHER PUBLICATIONS

Amirkhani et al., "Quantitation of tryptophan, kynurenine and kynurenic acid in human plasma by capillary liquid chromatography-electrospray ionization tandem mass spectrometry," *Journal of Chromatography B*, 780:381-387 (2002).

Rubio et al., "Cerebrospinal fluid carnitine levels in patients with Alzheimer's disease," *Journal of Neurological Sciences*, 155:192-195 (1998).

Shah et al., "Amino acid neurotransmitters: separation approaches and diagnostic value," *Journal of Chromatography B*, 781:151-163 (2002).

von Kienlin et al., "Altered metabolic profile in the frontal cortex of PS2APP transgenic mice, monitored throughout their life span," *Neurobiology of Disease*, 18: 32-39 (2005).

Alkondon et al., "Targeted deletion of the kynurenine aminotransferase II gene reveals a critical role of endogenous kynurenic acid in the regulation of synaptic transmission via alpha-7 nicotinic receptors in the hippocampus," J. Neuroscience, 24(19)4635-48 (2004).

*Primary Examiner* — Christine T Mui
(74) *Attorney, Agent, or Firm* — K&L Gates LLP

(57) ABSTRACT

Markers are provided that are predictive of Alzheimer's disease. Levels of these markers, when different from a standard, are indicative of a patient being at risk of having or developing Alzheimer's disease.

32 Claims, 9 Drawing Sheets

METHODS FOR DETECTING ALZHEIMER'S DISEASE

CROSS-REFERENCE TO RELATED APPLICATION

This application is the national phase of International (PCT) Patent Application Serial No. PCT/US2006/009042, filed on Mar. 13, 2006, which claims priority to and the benefit of U.S. Provisional Patent Application Ser. No. 60/661,393, filed on Mar. 14, 2005, the entire disclosures of which are incorporated by reference herein.

FIELD OF THE INVENTION

The invention relates to methods for detecting Alzheimer's disease. More specifically, the invention relates to methods for screening an individual for being at risk of having or developing Alzheimer's disease by using two or more markers.

BACKGROUND

Alzheimer's disease afflicts more than four million people in the United States, and this number is expected to double during the next forty years with the aging of the population. After heart disease, cancer, and stroke, Alzheimer's disease is the fourth leading cause of death among the elderly in developed nations. Alzheimer's disease is a complex multi-genic neurodegenerative disorder characterized by progressive impairments in memory, behavior, language, and visuo-spatial skills, ending ultimately in death. Hallmark pathologies of Alzheimer's disease include granulovascular neuronal degeneration, extracellular neuritic plaques with beta-amyloid deposits, intracellular neurofibrillary tangles and neurofibrillary degeneration, synaptic loss, and extensive neuronal cell death. It is now known that these histopathologic lesions of Alzheimer's disease correlate with the dementia observed in many elderly people.

Although Alzheimer's disease is one of the most common types of dementia among the elderly, it is difficult to diagnose because Alzheimer's-like symptoms are common to many other diseases (e.g., AIDS, brain cancer, Parkinson's disease, and deficiencies of vitamin E, magnesium, and B vitamins). Generally, the only definite diagnosis comes from a postmortem biopsy of the diseased brain.

Over one hundred billion dollars are spent annually on Alzheimer's disease, making it the third most costly disease in the United States after heart disease and cancer. Much of this cost is related to caregiving, such as nursing home care and in-home day care. Accordingly, to the extent Alzheimer's disease could be affirmatively diagnosed during an individual's lifetime, medical treatment might be provided that might provide benefits by slowing the rate of cognitive decline, delaying institutionalization, reducing caregiver hours, and improving quality of life.

Early detection and identification of Alzheimer's disease is necessary to facilitate prompt, appropriate treatment and care. Currently, there is no laboratory diagnostic test for Alzheimer's disease. As stated above, the only true existing diagnosis is made by pathologic examination of postmortem brain tissue in conjunction with a clinical history of dementia. This diagnosis is based on the presence in brain tissue of neuritic (senile) plaques and of neurofibrillary tangles, which have been correlated with clinical dementia. The neurohistopathologic identification and counting of neuritic plaques and neurofibrillary tangles requires staining and microscopic examination of several brain sections. However, the results of this methodology can vary widely and is time-consuming and labor-intensive.

Thus, there remains a need for diagnostic methods for Alzheimer's disease. In particular, reliable and cost-effective methods and compositions are needed to allow for diagnosis of Alzheimer's disease.

SUMMARY OF THE INVENTION

Markers have been identified that are predictive of Alzheimer's disease. The levels of these markers, when different from a standard, are indicative of Alzheimer's disease. Methods according to the invention utilize some or all of the markers to detect Alzheimer's disease. Specifically, an individual can be screened for being at risk of having or developing Alzheimer's disease by using two or more of these markers and determining if the levels of these markers are different from a standard.

Fourteen (first-choice) markers have been identified that can be chosen to create assays of varying specificity and sensitivity for detecting Alzheimer's disease. Specificity is the true negative rate, or the screening test's ability to correctly identify the absence of disease. In other words, it is the percentage of people in a group who truly do not have the disease. A test with high specificity has few false positives. Sensitivity is the true positive rate, or the screening test's ability to identify true disease. In other words, it is the percentage of people in a group who are detected as positives who truly are positive for the disease. A test with high sensitivity has few false negatives. Typically, the more markers that are used in the assay, the better the sensitivity and the specificity of the assay. Specifically, when all fourteen (first-choice) markers are used, a sensitivity of about 82.6% and a specificity of about 92.6% can be obtained.

The markers of the present invention can be useful for more than just diagnosing Alzheimer's disease. The markers can be used to screen candidate drugs for treating Alzheimer's disease or to determine the efficacy of a drug treatment on an individual with Alzheimer's disease. The markers also can be used to identify individuals whose health needs to be monitored. Also, the markers can be used to validate an animal model for Alzheimer's disease.

In one aspect, the invention provides a method for screening an individual for being at risk of having or developing Alzheimer's disease. An amount of each at least two markers in a sample from a patient are compared with each of the at least two markers from a standard. A difference in the amount of each of the at least two markers between the sample and the standard indicates a positive screen. The at least two markers are selected from a group of molecules. Each molecule of the group is characterized by a liquid chromatography retention time ("LCRT") and mass-to-charge ratio ("MCR") pair as set forth in Table 1 below.

TABLE 1

Molecule Characterizations.

| Row Number | Liquid Chromatography Retention Time (minutes) | Mass-to-charge Ratio |
|---|---|---|
| 1 | 3.42 | 169 |
| 2 | 10.45 | 246 |
| 3 | 17.14 | 120 |
| 4 | 22.05 | 202 |
| 5 | 10.66 | 254 |
| 6 | 17.98 | 273 |

TABLE 1-continued

Molecule Characterizations.

| Row Number | Liquid Chromatography Retention Time (minutes) | Mass-to-charge Ratio |
|---|---|---|
| 7 | 19.44 | 260 |
| 8 | 8.39 | 153 |
| 9 | 16.07 | 203 |
| 10 | 16.12 | 245 |
| 11 | 10.20 | 218 |
| 12 | 19.29 | 304 |
| 13 | 10.50 | 227 |
| 14 | 16.33 | 333 |
| 15 | 3.48 | 336 |
| 16 | 11.24 | 229 |
| 17 | 17.09 | 222 |
| 18 | 14.57 | 297 |
| 19 | 9.03 | 176 |
| 20 | 11.31 | 274 |
| 21 | 19.41 | 261 |
| 22 | 8.47 | 153 |
| 23 | 15.96 | 220 |
| 24 | 16.05 | 231 |
| 25 | 17.66 | 288 |
| 26 | 23.10 | 304 |
| 27 | 11.27 | 141 |
| 28 | 12.23 | 277 |
| 29 | 14.59 | 278 |
| 30 | 13.13 | 247 |
| 31 | 15.75 | 188 |
| 32 | 19.84 | 304 |
| 33 | 12.59 | 130 |
| 34 | 11.35 | 273 |
| 35 | 19.48 | 186 |
| 36 | 18.24 | 303 |
| 37 | 19.47 | 260 |
| 38 | 10.49 | 254 |
| 39 | 14.20 | 218 |
| 40 | 12.38 | 248 |
| 41 | 11.26 | 197 |
| 42 | 15.09 | 261 |
| 43 | 9.13 | 175 |
| 44 | 10.60 | 185 |
| 45 | 12.71 | 205 |
| 46 | 17.65 | 257 |
| 47 | 15.55 | 265 |
| 48 | 19.34 | 368 |

The chromatography retention time is determined by a high performance liquid chromatography system ("HPLCS"). The HPLCS includes a stationary phase and a mobile phase. The stationary phase includes a $C_{18}$ guard column and a reverse-phase $C_{18}$ chromatography column. The $C_{18}$ guard column has an inner diameter of 10 mm and a length of 50 mm and includes ocadecyl-bonded silica particles with a mean diameter of about 5 µm. The reverse-phase $C_{18}$ chromatography column has an inner diameter of 3 mm and a length of 100 mm and includes ocadecyl-bonded silica particles with a mean diameter of about 5 µm. The mobile phase includes solvent A and solvent B. Solvent A varies from 0% to 100% by volume of the mobile phase and is a 0.1% aqueous formic acid solution. The Solvent B varies from 0% to 100% by volume of the mobile phase and is 80% by volume acetonitrile and 20% by volume of a 0.1% aqueous formic acid solution.

The mobile phase passes through the stationary phase at ambient temperature and at a rate of 0.3 milliliters per minute. Initially, the ratio of solvent A to solvent B decreases linearly from 100:0 to 95:5 over 2.50 minutes. The ratio of solvent A to solvent B then decreases linearly from 95:5 to 60:40 over the next 17.5 minutes. The ratio of solvent A to solvent B then decreases linearly from 60:40 to 0:100 over the next 2.00 minutes. Then, the ratio of solvent A to solvent B is maintained at 0:100 over the next 8.00 minutes. The mass-to-charge ratio is determined by a mass spectrometry system including an electrospray ion source and a quadruple ion trap detector scanning in the positive ion mode.

This aspect of the invention can have any or all of the following features. In various embodiments of the method, the amount of each of at least three markers can be compared, the amount of each of at least four markers can be compared, the amount of each of at least five markers can be compared, the amount of each of at least six markers can be compared, the amount of each of at least seven markers can be compared, the amount of each of at least eight markers can be compared, the amount of each of at least nine markers can be compared, the amount of each of at least ten markers can be compared, the amount of each of at least eleven markers can be compared, the amount of each of at least twelve markers can be compared, the amount of each of at least thirteen markers can be compared, or the amount of each of at least fourteen markers can be compared. The first marker and second marker can be molecules characterized by the LCRT and MCR pair as set forth in row numbers 1 and 2 of Table 1. The third marker can be a molecule characterized by the LCRT and MCR pair as set forth in row number 3 of Table 1. The fourth marker can be a molecule characterized by the LCRT and MCR pair as set forth in row number 4 of Table 1.

In another aspect, the invention provides a method for screening an individual for being at risk of having or developing Alzheimer's disease. An amount of each at least two markers in a sample from a patient are compared with each of the at least two markers from a standard. A difference in the amount of each of the at least two markers between the sample and the standard indicates a positive screen. The markers are selected from phenylalanine, glutamate, carnitine, urate, L-homocitrulline, 4-methylene-glutamate, 4-acetamidobutanoate, 6-amino-2-oxohexanoate, (S)-5-amino-3-oxohexanoate, L-2-aminoadipate-6-semialdehyde, 2-amino-3-oxohexanoate, N4 acetylaminobutanoate, 2-oxo-hex-trans-4-enoate, nicotinurate, N-acetyl histidine, N-formimino-L-aspartate, cis-aconitate, trans-aconitate, tyrosine ethyl ester, 3-hydroxy-anthranilate, 3-hydroxy-2-methylpyridine-5-carboxylate, 4-amino-salicylate, 1-carbapen-2-em-3-carboxylic acid, saccaropine, 2-(hydroxymethyl)-3-(acetamidomethylene) succinate, and butyl esters thereof.

In various embodiments of this aspect of the method, the amount of each of at least three markers can be compared, the amount of each of at least four markers can be compared, the amount of each of at least five markers can be compared, the amount of each of at least six markers can be compared, the amount of each of at least seven markers can be compared, the amount of each of at least eight markers can be compared, the amount of each of at least nine markers can be compared, the amount of each of at least ten markers can be compared, the amount of each of at least eleven markers can be compared, the amount of each of at least twelve markers can be compared, the amount of each of at least thirteen markers can be compared, or the amount of each of at least fourteen markers can be compared.

In another aspect, the invention provides a method for screening an individual for being at risk of having or developing Alzheimer's disease. An amount of each at least two markers in a sample from a patient are compared with each of the at least two markers from a standard. A difference in the amount of each of the at least two markers between the sample and the standard indicates a positive screen. The first marker is selected from a group of molecules, each molecule of the group characterized by the LCRT and MCR pair as set forth in row numbers 1, 15, and 29 of Table 1. The second marker is selected from a group of molecules, each molecule of the group characterized by the LCRT and MCR pair as set forth in row numbers 2, 16, and 30 of Table 1. The LCRT and MCR pairs for each molecule is determined by HPLCS as recited above.

This aspect of the invention can have any or all of the following features. The at least two markers can include a third marker selected from a group of molecules, each molecule of the group characterized by a LCRT and MCR pair as set forth in row numbers 3, 17, and 31 on Table 1. The at least two markers can include a fourth marker selected from a group of molecules, each molecule of the group characterized by the LCRT and MCR pair as set forth in row numbers 4, 18, and 32 on Table 1. The at least two markers can include a fifth marker selected from a group of molecules, each molecule of the group characterized by the LCRT and MCR pair as set forth in row numbers 5, 19, and 33 on Table 1. The at least two markers can include a sixth marker selected from a group of molecules, each molecule of the group characterized by the LCRT and MCR pair as set forth in row numbers 6, 20, and 34 on Table 1. The at least two markers can include a seventh marker selected from a group of molecules, each molecule of the group characterized by the LCRT and MCR pair as set forth in row numbers 7, 21, and 35 on Table 1. The at least two markers can include an eighth marker selected from a group of molecules, each molecule of the group characterized by the LCRT and MCR pair as set forth in row numbers 8, 22, and 36 on Table 1. The at least two markers can include a ninth marker selected from a group of molecules, each molecule of the group characterized by the LCRT and MCR pair as set forth in row numbers 9, 23, and 37 on Table 1. The at least two markers can include a tenth marker selected from a group of molecules, each molecule of the group characterized by the LCRT and MCR pair as set forth in row numbers 10, 24, and 38 on Table 1. The at least two markers can include an eleventh marker selected from a group of molecules, each molecule of the group characterized by the LCRT and MCR pair as set forth in row numbers 11, 25, and 39 on Table 1. The at least two markers can include a twelfth marker selected from a group of molecules, each molecule of the group characterized by the LCRT and MCR pair as set forth in row numbers 12, 26, and 40 on Table 1. The at least two markers can include a thirteenth marker selected from a group of molecules, each molecule of the group characterized by the LCRT and MCR pair as set forth in row numbers 13, 27, and 41 on Table 1. The at least two markers can include a fourteenth marker selected from a group of molecules, each molecule of the group characterized by the LCRT and MCR pair as set forth in row numbers 14, 28, and 42 on Table 1.

In another aspect, the invention provides a method for screening an individual for being at risk of having or developing Alzheimer's disease. An amount of each at least two markers in a sample from a patient are compared with each of the at least two markers from a standard. A difference in the amount of a statistically significant number of the at least two markers between the sample and the standard indicates a positive screen. The at least two markers are selected from a group of molecules. Each molecule of the group is characterized by a liquid chromatography retention time ("LCRT") and mass-to-charge ratio ("MCR") pair as set forth in Table 1. The LCRT and MCR pair for each molecule is determined by HPLCS as recited above.

This aspect of the invention can have any or all of the following features. The statistically significant number of markers can be two, three, four, five, six, seven, eight, nine, ten, eleven, twelve, thirteen, or fourteen. The screen can be characterized by a specificity of at least about 50%, at least about 60%, at least about 70%, at least about 80%, or at least about 90%. The screen can be characterized by a sensitivity of at least about 50%, at least about 60%, at least about 70%, at least about 80%, or at least about 90%. The first marker and second marker can include molecules characterized by the LCRT and MCR pair as set forth in row numbers 1 and 2 of Table 1. The third marker can include a molecule characterized by the LCRT and MCR pair as set forth in row number 3 of Table 1. The fourth marker can include a molecule characterized by the LCRT and MCR pair as set forth in row number 4 of Table 1.

In another aspect, the invention provides a method for screening an individual for being at risk of having or developing Alzheimer's disease. An amount of each at least two markers in a sample from a patient are compared with each of the at least two markers from a standard. A difference in the amount of a statistically significant number of the at least two markers between the sample and the standard indicates a positive screen. The markers are selected from phenylalanine, glutamate, carnitine, urate, L-homocitrulline, 4-methyleneglutamate, 4-acetamidobutanoate, 6-amino-2-oxohexanoate, (S)-5-amino-3-oxohexanoate, L-2-aminoadipate-6-semialdehyde, 2-amino-3-oxohexanoate, N4 acetylaminobutanoate, 2-oxohex-trans-4-enoate, nicotinurate, N-acetyl histidine, N-formimino-L-aspartate, cis-aconitate, trans-aconitate, tyrosine ethyl ester, 3-hydroxy-anthranilate, 3-hydroxy-2-methylpyridine-5-carboxylate, 4-amino-salicylate, 1-carbapen-2-em-3-carboxylic acid, saccaropine, 2-(hydroxymethyl)-3-(acetamidomethylene) succinate, and butyl esters thereof.

This aspect of the invention can have any or all of the following features. The statistically significant number of markers can be two, three, four, five, six, seven, eight, nine, ten, eleven, twelve, thirteen, or fourteen. The screen can be characterized by a specificity of at least about 50%, at least about 60%, at least about 70%, at least about 80%, or at least about 90%. The screen can be characterized by a sensitivity of at least about 50%, at least about 60%, at least about 70%, at least about 80%, or at least about 90%.

Various methods can be used for detecting the amount of each of the at least two markers in any of the aspects as described above, including immunoassay, mass spectroscopy, chromatography, chemical analysis, a colorimetric assay, spectrophotometric analysis, electrochemical analysis, and nuclear magnetic resonance. It is contemplated, however, that other analytical methods may be useful in the detection of the markers as well. Additionally, the methods described above and throughout the specification, can be performed on samples including a body fluid sample. For example, the methods of the invention may be performed on whole blood, blood plasma, blood serum, cerebrospinal fluid, saliva, urine, seminal fluid, breast nipple aspirate, pancreatic fluid, and combinations thereof. It is contemplated, however, that the methods of the invention also may be useful in detecting the markers in other body fluid samples or tissue samples. Additionally, the standard can be obtained from at least one healthy person, the healthy person having a predetermined dietary intake for a predetermined time before sampling. Moreover, the sample can be obtained from a patient of the same sex as the at least one healthy person, the patient having the same predetermined dietary intake for the same predetermined time before sampling as the at least one healthy person.

BRIEF DESCRIPTION OF THE DRAWINGS

The foregoing and other objects, features, and advantages of the invention described above will be more fully understood from the following description of various illustrative embodiments, when read together with the accompanying drawings. In the drawings, like reference characters generally refer to the same parts throughout the different views. The drawings are not necessarily to scale, and emphasis instead is generally placed upon illustrating the principles of the invention.

DETAILED DESCRIPTION

Figure 1:
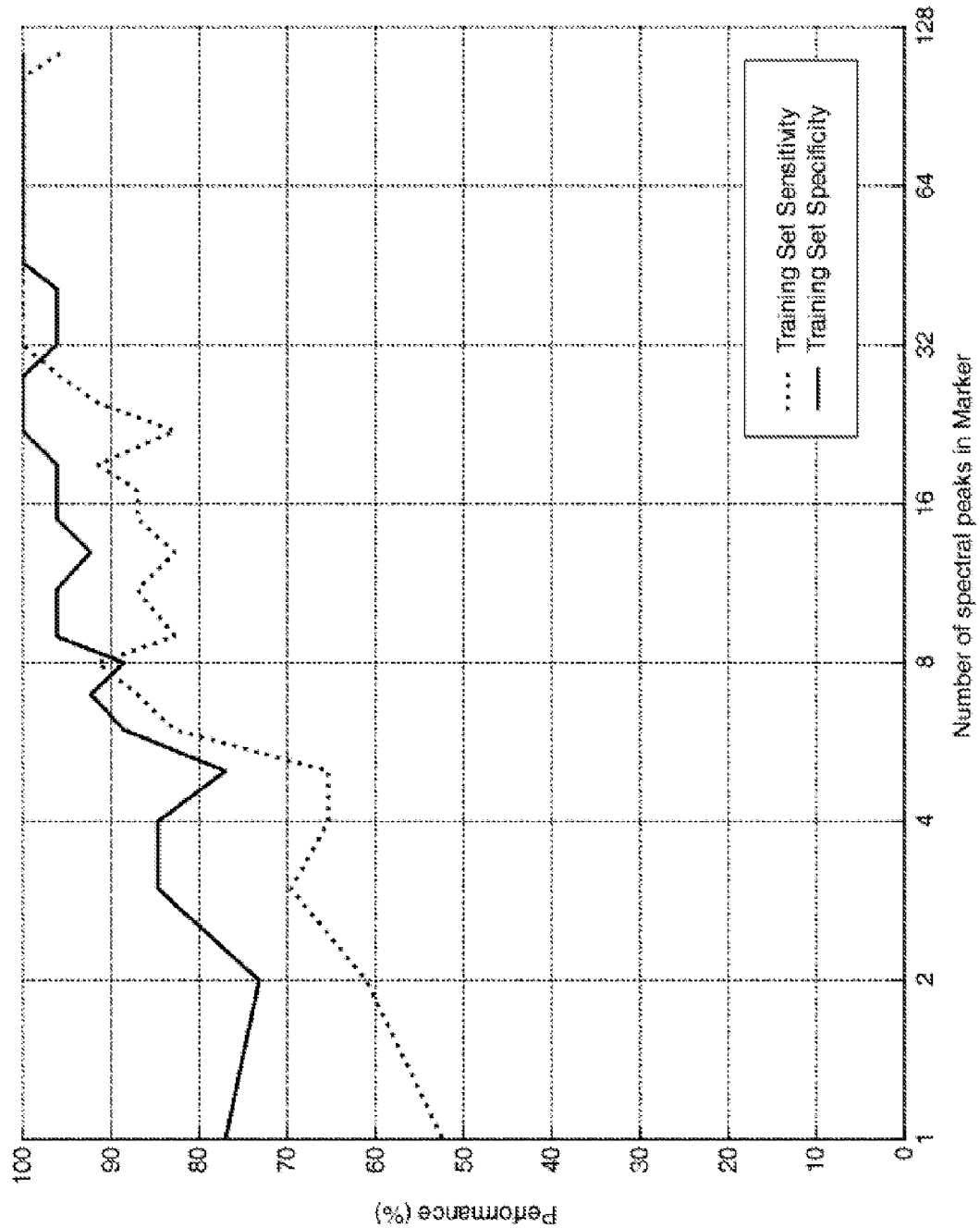
FIG. 1 shows an exemplary plot of the "Training Performance" on data sets as a function of the number of markers.

Markers have been identified that are predictive of Alzheimer's disease. When two or more of these markers are present in a body fluid sample from an individual in amounts different than those in a standard, they are indicative that the individual is at risk of having or developing Alzheimer's disease.

Fourteen (first-choice) markers have been identified. Certain methods according to the invention utilize two or more of these markers to detect Alzheimer's disease. Specifically, a sample from an individual can be screened to determine whether the sample contains levels of two or more of each of these markers that are different from a standard sample. If the sample contains an amount of each of two or more of these markers that is different from the amount of these markers in a standard, the screen is considered a "positive screen" (i.e., the individual is at risk of having or developing Alzheimer's disease). Greater sensitivity and specificity in classifying Alzheimer's disease samples can be obtained, typically, by using a greater number of the fourteen markers. The samples potentially containing these markers can be drawn from multiple biological sample types (e.g., body fluids, tissue, cells) obtained from multiple sources (e.g., whole blood, blood plasma, blood serum, urine, cerebrospinal fluid, epithelial cells, and endothelial cells). It should be understood that all possible combinations of the markers disclosed herein (and not just the fourteen (first-choice) markers) can be used in methods according to the invention.

Using the methodology described more fully in Example 1, the fourteen (first-choice) markers were identified. Briefly, through a specific analytical classification protocol, a set of spectral peaks were obtained. These peaks characterize specific molecules. Utilizing these peaks (which include many more peaks than just fourteen), fourteen (first-choice) peaks were identified (as well as other preferred peaks as described below). Insofar as peaks characterize molecules, identifying fourteen (first-choice) peaks from among a much larger number of peaks means that the markers are chosen from a group of molecules including more than the fourteen molecules corresponding to the fourteen (first-choice) markers. The markers (i.e., the molecules) may be any type of a molecule. The markers (molecules) include, but are not limited to, proteins, peptides, amino acids, lipids, steroids, nucleic acids, metabolites and elements. Table 2 provides specific analytical data identifying the fourteen (first-choice) peaks (i.e., identifying the chosen markers). Because these peaks were generated twice, the identification of the fourteen markers from each run (i.e., "Run 1" and "Run 2") are provided. A comparison of the peaks indicates that the results are reproducible. Each peak is identified according to a specific format, "ABC.DEFG", where ABC its mass-to-charge ratio ("MCR") and DE.FG minutes is the liquid chromatographic retention time ("LCRT"). For example, the notation in the first entry of Run 1, "169.0342", indicates that the identified spectral peak has an MCR of 169 and a LCRT of 3.42 minutes. The identified molecules were verified using Fourier-transform mass spectrometry to calculate elemental composition from accurate mass measurements, as well as by evaluation with reference compounds. The "weight" of each peak is a mathematical construct with arbitrary units that can be used to rank order the peaks regarding their strength in classifying AD patients. The final column of Table 2 rank-orders the peaks by weight. Accordingly, the highest weight peak is ranked number 1 and the lowest weight peak is ranked number 14.

TABLE 2

Peak identifications from two experimental runs.

| Peak ID in Run 2 | Peak ID in Run 1 | Weight | Rank by weight |
| --- | --- | --- | --- |
| 169.0348 | 169.0342 | 2.88 | 1 |
| 246.1035 | 246.1045 | 2.70 | 2 |
| 120.1708 | 120.1714 | 2.67 | 3 |
| 202.2312 | 202.2205 | 2.35 | 4 |
| 254.1049 | 254.1066 | 2.31 | 5 |
| 273.1889 | 273.1798 | 2.21 | 6 |
| 260.1947 | 260.1944 | 2.18 | 7 |
| 153.0827 | 153.0839 | 1.69 | 8 |
| 203.1596 | 203.1607 | 1.45 | 9 |
| 245.1699 | 245.1612 | 1.39 | 10 |
| 218.0981 | 218.1020 | 1.32 | 11 |
| 304.1984 | 304.1929 | 1.28 | 12 |
| 227.1045 | 227.1050 | 0.59 | 13 |
| 333.1642 | 333.1633 | 0.55 | 14 |

Table 3 summarizes the performance of the fourteen (first-choice) markers in segregating AD from CTRL samples as a function of the number of markers (and, specifically, the "Test Performance" more fully described in Example 1). The values in parentheses are the standard errors ("SE") that were calculated based on the underlying binomial distribution of total numbers of AD and CTRL samples correctly classified. These fourteen markers, when taken together, achieve a sensitivity performance of 82.6% and specificity performance of 92.5% in classifying AD and CTRL subjects. The row of Table 3 having one peak corresponds with the highest weighted peak in Table 2, and the row of Table 3 having two peaks corresponds to the highest weighted peaks in Table 2 The remainder of the rows of Table 2 and 3 are similarly related. Accordingly, if the thirteen best (or highest weighted) markers are chosen (i.e., leaving out the marker having the lowest weight as described for Table 2, above), the sensitivity performance remains at 82.6% and the specificity performance falls slightly to 92.0%. This result is shown in the row for 13 peaks. The rest of the table is read in this manner. For example, the row for 12 peaks indicates sensitivity and specificity for the 12 best (highest weight) markers, leaving out the two lowest weight markers.

TABLE 3

Fourteen (first-choice) markers and their classification performance.

| Number of Peaks | Test Sensitivity and SE (%) | Test Specificity And SE (%) |
|---|---|---|
| 14 | 82.6 (10.2) | 92.6 (8.3) |
| 13 | 82.6 (9.4) | 92.0 (8.2) |
| 12 | 77.1 (10.5) | 85.2 (9.6) |
| 11 | 75.0 (10.1) | 82.1 (9.3) |
| 10 | 75.0 (11.2) | 85.2 (9.5) |
| 9 | 81.8 (13.4) | 76.7 (9.2) |
| 8 | 72.9 (10.4) | 85.2 (9.7) |
| 7 | 73.8 (10.5) | 74.2 (9.1) |
| 6 | 69.2 (10.3) | 69.7 (9.4) |
| 5 | 69.2 (12.0) | 76.7 (9.1) |
| 4 | 72.9 (11.4) | 79.3 (9.9) |
| 3 | 77.1 (13.2) | 69.7 (12.2) |
| 2 | 75.0 (11.7) | 74.2 (11.6) |
| 1 | 55.1 (12.4) | 62.1 (11.6) |

As stated above, the identity of the molecule making up the marker is uniquely characterized and identified by a spectral peak described above. Notwithstanding the fact that the markers have been affirmatively identified, for any particular peak, it may be that it is difficult to identify, by name, a peak that is already analytically defined, may be that the marker is a biologically non-significant molecule (such as a contaminant or an internal standard), or may be that the peak is duplicative with another peak. Accordingly, at least two approaches are available to address these issues. The first approach is to substitute another peak for the original peak that resists full identification or is otherwise insignificant. The substitute peak is statistically highly correlated with the original peak. In this instance, classification performance may be slightly altered. Typically, the more substitutions that are made, the more the performance is altered from those shown in Table 3. Table 4 provides a list of the original peaks (the fourteen first-choice peaks) as well as the first choice and second choice substitute peaks. These peaks are grouped by row in Table 4. The first choice substitute peaks are the peaks having the highest correlation with the original fourteen peaks. Accordingly, for example, if the original peak from row number 1 cannot be used for some reason, the first choice substitute peak from row number 1 is substituted. The second choice peaks are the peaks with the next highest correlation with the original peaks. Accordingly, for example, if the original peak and first choice substitute peak from the row number 1 cannot be used for some reason, then the second choice substitute peak is substituted. It should be understood that this discussion uses "peak" as a proxy for the chosen marker. As such, Table 4 actually shows which markers should be substituted for any of the original fourteen (first-choice) markers. Furthermore, because of the high correlation between these markers, in actuality, any of the markers identified in Table 4 can be used irrespective of whether substitution is needed (for example, in combination with any markers described herein and with any number of the markers described herein).

TABLE 4

Substitute peaks for original peaks.

| Row Number | Original Peak | Substitute Peak- First Choice | Substitute Peak- Second Choice |
|---|---|---|---|
| 1 | 169.0348 | 336.0348 | 278.1459 |
| 2 | 246.1035 | 229.1124 | 247.1313 |
| 3 | 120.1708 | 222.1709 | 188.1575 |
| 4 | 202.2312 | 297.1457 | 304.1984 |
| 5 | 254.1049 | 176.0903 | 130.1259 |
| 6 | 273.1889 | 274.1131 | 273.1135 |
| 7 | 260.1947 | 261.1941 | 186.1948 |
| 8 | 153.0827 | 153.0847 | 303.1824 |
| 9 | 203.1596 | 220.1596 | 260.1947 |
| 10 | 245.1699 | 231.1605 | 254.1049 |
| 11 | 218.0981 | 288.1766 | 218.1420 |
| 12 | 304.1984 | 304.2310 | 248.1238 |
| 13 | 227.1045 | 141.1127 | 197.1126 |
| 14 | 333.1642 | 277.1223 | 261.1509 |

The second approach is to substitute peaks with those which were ranked lower than the top fourteen (i.e., peaks having a weight less than the top fourteen peaks). The peaks ranked fifteenth through twenty-fourth are listed in Table 5. This method of substitution would require a new classifier to be constructed (according to the principles provided in Example 1). The change in classification performance due to this substitution will depend on issues including whether the original peak was a highly-weighted one and on the weight of the substitute peak. Although the first substitution approach discussed above is preferred, this strategy also can be used. Again, it should be understood that this discussion uses "peak" as a proxy for the marker it identifies. As such, Table 5 shows markers that can be substituted for any of the original (first-choice) markers. Furthermore, any of the markers in Table 5 can be used irrespective of whether substitution is needed (for example in combination with any marker described herein and with any number of the markers described herein).

TABLE 5

Substitute Peaks beyond the original, first choice substitute, and second choice substitute peaks.

| Ranking | Peaks |
|---|---|
| 15 | 130.1259 |
| 16 | 175.0913 |
| 17 | 185.1060 |
| 18 | 205.1271 |
| 19 | 247.1313 |
| 20 | 257.1765 |
| 21 | 261.1509 |
| 22 | 265.1555 |
| 23 | 297.1457 |
| 24 | 368.1934 |

Now that the markers (i.e., any of the fourteen first-choice markers or the substitute markers) are known, they can be used to screen an individual to determine whether the amount of each of two or more of these markers in a sample from the individual is different from the amount of each of the two or more markers from a standard, classifying the individual, to a certain specificity and sensitivity, as having or being at risk of developing Alzheimer's disease. Based on the number of markers examined, the desired sensitivity and specificity of the assay can be chosen (e.g., Table 2). The standard can be an actual sample or previously-generated empirical data. The standard can be obtained from a known normal person. The known normal person can be a healthy person and can have a predetermined dietary intake for a predetermined time before sampling. Moreover, the sample can be obtained from a known normal person of the same sex as the patient. Alternatively, the markers could be compared to those of a known AD patient, in which case the similarity between the two samples would be examined. Various techniques and/or kits can be used by a medical professional for screening patient samples in order to determine the level and/or amount of a particular marker in a patient sample. Examples of such assays are described below and include, but are not limited to, an immunoassay, mass spectroscopy, chromatography, a chemical analysis, a colormetric assay, a spectrophotometric analysis, an electrochemical analysis, and nuclear magnetic resonance. Additionally, such assays can be performed on any biological sample including whole blood, blood plasma, blood serum, cerebrospinal fluid, saliva, urine, seminal fluid, breast nipple aspirate, pancreatic fluid, and combinations thereof. These assays are chosen based on which are best suited to detect a particular marker as well as which are best suited for use with a particular biological sample. Accordingly, multiple assays may be used to detect the desired markers, and samples may be analyzed from one or more sources.

A marker can be detected and/or quantified by using one or more separation methods. For example, suitable separation methods may include a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APC)-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, fourier transform mass spectrometry (FTMS) and ion trap. Spectrometric techniques that can also be used include resonance spectroscopy and optical spectroscopy.

Other suitable separation methods include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE), or other chromatographic techniques, such as thin-layer, gas or liquid chromatography, or any combination thereof. In one embodiment, the biological sample to be assayed may be fractionated prior to application of the separation method.

Tandem linking of chromatography (for example liquid chromatography ("LC") and mass spectrometry ("MS") is useful for detecting and quantifying one or more of the markers. LC is used to separate the molecules, which may include a marker, in a sample from an individual. A small amount of the sample, dissolved in a solvent, is injected into the injection port of the LC device, which is kept at a high temperature. The LC column of the device contains a solid substrate that can be either polar or non-polar. Because of differing polarities of the molecules in the sample, the molecules will have differing affinities for the solid substrate in the column and will elute at different times. The stronger the affinity of the molecule to the substrate, the longer the retention time of the molecule in the column. As the molecules exit the column, they enter the mass spectrometer. The mass spectrometer ionizes the molecules. In the tandem mass spectrometry mode, if the system is standardized properly, each compound sent into a mass spectrometer fragments into ions of various masses and abundances forming a signature pattern unique to that substance. By comparing the tandem mass spectrograph of each peak to a computerized database, the computer is usually able to identify the molecules with a high degree of certainty. Alternately, or additionally, this comparison may be carried out by human inspection. Once an identity is established, the computer integrates the area under each peak and thereby determines the relative quantity of each molecule in the mixture. To the extent any of the molecules are identified as a marker, the amount of the marker is compared with the amount of the marker from a standard to determine if there is a difference.

A Markers also may be detected and/or quantified by methods that do not require physical separation of the markers themselves. For example, nuclear magnetic resonance (NMR) spectroscopy may be used to resolve a profile of a marker from a complex mixture of molecules. An analogous use of NMR to classify tumors is disclosed in Hagberg, NMR Biomed. 11: 148-56 (1998), for example. Additional procedures include nucleic acid amplification technologies, which may be used to determine a marker profile without physical separation of individual molecules. (See Stordeur et al., J. Immunol. Methods 259: 55-64 (2002) and Tan et al., Proc. Nat'l Acad. Sci. USA 99: 11387-11392 (2002), for example.)

A marker in a sample also may be detected and/or quantified, for example, by combining the marker with a binding moiety capable of specifically binding the marker. The binding moiety may include, for example, a member of a ligand-receptor pair, i.e., a pair of molecules capable of having a specific binding interaction. The binding moiety may also include, for example, a member of a specific binding pair, such as antibody-antigen, enzyme-substrate, nucleic acid-nucleic acid, protein-nucleic acid, protein-protein, or other specific binding pairs known in the art. Binding proteins may be designed which have enhanced affinity for a target. Optionally, the binding moiety may be linked with a detectable label, such as an enzymatic, fluorescent, radioactive, phosphorescent or colored particle label. The labeled complex may be detected, e.g., visually or with the aid of a spectrophotometer or other detector, and/or may be quantified.

A marker also may be detected and/or quantified using gel electrophoresis techniques available in the art. In two-dimensional gel electrophoresis, molecules are separated first in a pH gradient gel according to their isoelectric point. The resulting gel then is placed on a second polyacrylamide gel, and the molecules separated according to molecular weight (See, for example, O'Farrell *J. Biol. Chem.* 250: 4007-4021 (1975)). A marker for AD may be detected by first isolating molecules from a sample obtained from an individual suspected of having AD and then separating the molecules by two-dimensional gel electrophoresis to produce a characteristic two-dimensional gel electrophoresis pattern. The pattern may then be compared with a standard gel pattern produced by separating, under the same or similar conditions, molecules isolated from the standard (e.g., CTRL or AD subjects). The standard gel pattern may be stored in, and retrieved from, an electronic database of electrophoresis patterns. Thus, it is determined if the amount of the marker in the patient is different from the amount in the standard. The presence of a plurality, e.g., two to fourteen, AD markers on the two-dimensional gel in an amount different than a known normal standard indicates a positive screen for AD in the individual. The assay thus permits the detection and treatment of Alzheimer's disease.

A marker also may be detected and/or quantified using any of a wide range of immunoassay techniques available in the art. For example, sandwich immunoassay format may be used to detect and/or quantify a marker in a sample from a patient. Alternatively, conventional immuno-histochemical procedures may be, used for detecting and/or quantifying the presence of a marker in a sample using one or more labeled binding proteins.

In a sandwich immunoassay, two antibodies capable of binding a marker generally are used, e.g., one immobilized onto a solid support, and one free in solution and labeled with a detectable chemical compound. Examples of chemical labels that may be used for the second antibody include radioisotopes, fluorescent compounds, and enzymes or other molecules that generate colored or electrochemically active products when exposed to a reactant or enzyme substrate. When a sample containing the marker is placed in this system, the marker binds to both the immobilized antibody and the labeled antibody, to form a "sandwich" immune complex on the support's surface. The complexed marker is detected by washing away non-bound sample components and excess labeled antibody, and measuring the amount of labeled antibody complexed to the marker on the support's surface. Alternatively, the antibody free in solution, which can be labeled with a chemical moiety, for example, a hapten, may be detected by a third antibody labeled with a detectable moiety which binds the free antibody or, for example, the hapten coupled thereto.

Both the sandwich immunoassay and tissue immunohistochemical procedures are highly specific and very sensitive, provided that labels with good limits of detection are used. A detailed review of immunological assay design, theory and protocols can be found in numerous texts in the art, including Butt, W. R., *Practical Immunology*, ed. Marcel Dekker, New York (1984) and Harlow et al. *Antibodies, A Laboratory Approach*, ed. Cold Spring Harbor Laboratory (1988).

In general, immunoassay design considerations include preparation of antibodies (e.g., monoclonal or polyclonal antibodies) having sufficiently high binding specificity for the target to form a complex that can be distinguished reliably from products of nonspecific interactions. As used herein, the term "antibody" is understood to mean binding proteins, for example, antibodies or other proteins comprising an immunoglobulin variable region-like binding domain, having the appropriate binding affinities and specificities for the target. The higher the antibody binding specificity, the lower the target concentration that can be detected. As used herein, the terms "specific binding" or "binding specifically" are understood to mean that the binding moiety, for example, a binding protein, has a binding affinity for the target of greater than about $10^5$ $M^{-1}$, more preferably greater than about $10^7$ $M^{-1}$.

Antibodies to an isolated target marker which are useful in assays for detecting a Alzheimer's disease in an individual may be generated using standard immunological procedures well known and described in the art. See, for example *Practical Immunology*, supra. Briefly, an isolated marker is used to raise antibodies in a xenogeneic host, such as a mouse, goat or other suitable mammal. The marker is combined with a suitable adjuvant capable of enhancing antibody production in the host, and is injected into the host, for example, by intraperitoneal administration. Any adjuvant suitable for stimulating the host's immune response may be used. A commonly used adjuvant is Freund's complete adjuvant (an emulsion comprising killed and dried microbial cells and available from, for example, Calbiochem Corp., San Diego, or Gibco, Grand Island, N.Y.). Where multiple antigen injections are desired, the subsequent injections may comprise the antigen in combination with an incomplete adjuvant (e.g., cell-free emulsion). Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target and have the desired binding affinity.

Antibody binding domains also may be produced biosynthetically and the amino acid sequence of the binding domain manipulated to enhance binding affinity with a preferred epitope on the target. Specific antibody methodologies are well understood and described in the literature. A more detailed description of their preparation can be found, for example, in *Practical Immunology*, (supra).

In addition, genetically engineered biosynthetic antibody binding sites, also known in the art as BABS or sFv's, may be used to determine if a sample contains a marker. Methods for making and using BABS comprising (i) non-covalently associated or disulfide bonded synthetic VH and VL dimers, (ii) covalently linked VH-VL single chain binding sites, (iii) individual VH or VL domains, or (iv) single chain antibody binding sites are disclosed, for example, in U.S. Pat. Nos. 5,091,513; 5,132,405; 4,704,692; and 4,946,778. Furthermore, BABS having requisite specificity for the marker can be derived by phage antibody cloning from combinatorial gene libraries (see, for example, Clackson et al. *Nature* 352: 624-628 (1991)). Briefly, phages, each expressing on their coat surfaces BABS having immunoglobulin variable regions encoded by variable region gene sequences derived from mice pre-immunized with an isolated marker, or a fragment thereof, are screened for binding activity against the immobilized marker. Phages which bind to the immobilized marker are harvested and the gene encoding the BABS is sequenced. The resulting nucleic acid sequences encoding the BABS of interest then may be expressed in conventional expression systems to produce the BABS protein.

An isolated marker also may be used for the development of diagnostic and other tissue evaluating kits and assays to monitor the level of the marker in a tissue or fluid sample. For example, the kit may include antibodies or other specific binding proteins which bind specifically to one or more markers and which permit the presence and/or amount of the one or more markers to be detected and/or quantified in a tissue or fluid sample.

Suitable kits for detecting one or more markers are contemplated to include, but are not limited to, a receptacle or other means for capturing a sample to be evaluated and a means for detecting the presence and/or amount in the sample of one or more of the markers described herein. Means for detecting in one embodiment includes, but is not limited to, one or more antibodies specific for these markers and means for detecting the binding of the antibodies to these markers by, for example, a standard sandwich immunoassay as described herein. Where the presence of a marker located within a cell is to be detected (e.g., as from a tissue sample) the kit also may comprise means for disrupting the cell structure so as to expose intracellular components.

The markers of the invention may include nucleic acids of a particular sequence. One or more of the markers may be detected and/or quantified by determining an amount of the marker nucleic acid in a sample, using, for example, Real-Time Quantitative PCR(RT-PCR) and comparing the measured amount to a standard. RT-PCR effectively measures the amount of a marker nucleic acid resulting from PCR. A positive result represents a measured amount of the marker nucleic acid that is different than the amount of the marker from a standard.

Primers can be developed that are complementary to the nucleic acid sequence of a particular nucleic acid marker. These primers direct a polymerase to copy and amplify that particular nucleic acid. RT-PCR detects the accumulation of the amplified nucleic acid marker during the reaction. During the exponential phase of the PCR reaction, the accumulating nucleic acid marker is measured. A calibration standard having a known concentration of nucleic acid is used to prepare a standard curve from which the quantity of the nucleic acid marker in the tested sample is extrapolated.

Once the amount of a nucleic acid marker in a sample is known, it can be compared to the amount of the marker from a standard. The standard for classification of AD patients can be determined by empirical means. For example, the amount can be determined by amplifying the nucleic acid marker in a sample from a population of one or more known normal individuals and quantitatively analyzing the amount of a nucleic acid marker in the population.

Also, additional forms of chemical analysis of a sample can be performed. For example, quantitative tests can be carried out that indicate the amounts of each marker in a sample. A colorimetric assay is a quantitative chemical analysis measuring color intensity produced by reacting a sample with a reactant as a proxy for the amount of the assayed material in a sample. Reagents can be provided that, when reacted with any marker, produce a color in the assay sample. The intensity of that color is dependent on the amount of the marker in the sample. By comparison of the intensity with a calibrated color card and/or standard, the amount of the marker in the sample can be determined. This amount can then be compared with the amount of the marker from a standard (such as from a known normal person).

Additionally, urinalysis can be used to determine the amount of a marker in a urine sample. Urine samples are tested with a variety of different instruments and techniques. Some tests use dipsticks, which are thin strips of plastic that change color in the presence of specific substances. Dipsticks could be used to measure the amount of a marker.

Not only does comparing the level of each of at least two markers to the level of each of the two markers from a standard allow for diagnosis of having or being at risk of having Alzheimer's disease, but this same comparison methodology can be adapted to other uses. For example, the markers could be used to screen candidate drugs for treating Alzheimer's disease. In this instance, treatment with candidate drugs would be monitored by monitoring the level of the markers. To the extent the markers returned to the standard level from the diseased level, efficacy could be determined. Moreover, with any drug that has already been found effective to treat Alzheimer's disease, it may be that certain patients may be responders and some may be non-responders. Accordingly, the markers could be monitored during treatment to determine if the drug is effective by determining if the level of the markers return to the standard level. Of course, there may not be any existing, known population of responders and non-responders, so that the efficacy of drug treatment on any Alzheimer's disease patient can be monitored over time. To the extent it is not efficacious, its use can be discontinued and another drug supplied in its place.

Moreover, comparing the level of each of at least two markers to the level of each of two markers from a standard can be done as a preventative screening measure and not just when cognitive deficit is observed (i.e., after the disease may have progressed). For example, assuming no evidence of cognitive decline, patients could be monitored after a certain age and at predetermined intervals in order to obtain a diagnosis of having or being at risk of having Alzheimer's disease at the earliest possible time. To the extent the screen is positive, a medical professional might recommend further monitoring for disease progression (either monitoring according to the invention or cognitive monitoring), and/or the medical professional might begin treatments with a drug or other therapy.

Moreover, the markers can be used to validate animal models of Alzheimer's disease. For example, in any particular model, a sample could be analyzed to determine if levels of the markers in the animal are the same as the levels of the markers in a known Alzheimer's disease patient. This would validate the model, for example, to test candidate drugs in the manner described above.

Example 1

This example describes the methodology used to identify markers for Alzheimer's disease. Briefly, bioanalytical and statistical analyses were conducted on urine of subjects diagnosed with Alzheimer's disease (AD), Control (CTRL) subjects, and Mild Cognitive Impairment subjects (MCI). As a result, unique spectral peaks that characterize molecules were generated. Following data manipulation and statistical analysis, a subset of these peaks was identified that could classify subjects as having AD or being CTRL with varying degrees of sensitivity. The molecules characterized by this subset of peaks were then designated as the markers of interest. Ultimately, a group of fourteen markers were shown to achieve the best specificity and sensitivity.

The spectral peaks were generated as follows. A liquid-chromatography ("LC")/mass spectrometry ("MS") analysis was performed using a high performance liquid chromatography system ("HPLCS") (an Alliance Waters 2690 separation module available from Waters Corp. of Milford, Mass.) and a mass spectrometry system comprising an electrospray ion source and a quadruple ion trap detector (an LCQ ion trap mass spectrometer available from ThermoFinnigan of San Jose, Calif.).

The following mixtures and reagents were prepared. Three "stock solutions" were prepared. As a chromatographic calibration internal standard ('IS'), one (1) mg d5-phenylalanine was added to 1 ml dimineralised water; 1 mg d3-gutamate was added to 1 ml dimineralised water; and 1 mg d3-leucine was added to 1 ml dimineralised water. An "IS-stock solution" was prepared by adding 100 μl of each of the 1 mg/ml stock solutions to 700 μl water (final concentration of 100 μg/ml). An "IS-work solution" was prepared by diluting 100 μl of the IS-stock solution to 1 ml with 900 μl of dimineralized water (final concentration of 10 μg/ml). "Solution A" was 300 mg/ml dithiothreitol (DTT). "Solution B" was Butanolis hydrochloric acid (prepared by adding 5 ml of 37% HCl (12N) to 15 ml of n-butanol). "Solution C" was 0.1% Formic acid and 1 mg/ml DTT in dimineralised water (prepared by adding 100 μl formic acid and 35 μl solution A to 100 ml dimineralised water).

Endogenous metabolites were extracted from urine samples and derivated using butanolic hydrochloric acid (solution B). Butylation was performed in order to block the carboxylic acid function of the amino acids and enhance the formation of protonated molecules, thereby increasing MS sensitivity. Three deuterated amino acids were added as an internal standard for quality control and scaling calculations. More specifically, the sample was prepared by first adding 10 μl of urine into a small vial with 10 μl of the IS-work solution and then vortexing briefly. Next, 10 μl of solution A was added to the vial, and the mixture was incubated for at least 30 minutes at room temperature. 100 μl of methanol (high-purity grade) was then added, and the mixture was centrifuged at 3500 relative centrifugal force ("rcf") for 5 minutes. The supernatant was collected and dried down under dry nitrogen. Next, 100 µl of solution B was added to the dried supernatant and vortexed briefly. The samples were next sealed and placed in an air oven and incubated at 65° for at least 60 minutes. The seal was then removed, and the excess HCL-butanol was evaporated to dryness under dry nitrogen. The derivative was then reconstituted in 100 µl of solution C. The sample was then analyzed using LC/MS.

The analysis was done using an HPLCS. The HPLCS included a stationary phase and a mobile phase. The stationary phase included a column and a guard column. The column used was a reverse-phase $C_{18}$ chromatography column having an inner diameter of 3 mm and a length of 100 mm and including octadecyl-bonded silica particles with a mean diameter of 5 µm (a Chrompack Inertsil® 5 µm ODS-3 100×3 mm from GL Sciences, Inc. of Japan). The guard column used was a $C_{18}$ guard column having an inner diameter of 10 mm and a length of 50 mm and including octadecyl-bonded silica particles with a mean diameter of 5 µm (a Chrompack Inertsil® 5 µm ODS-3 (S2) from GL Sciences, Inc. of Japan). The HPLCS also included an autosampler. The mobile phase included two solvents (Solvent A and Solvent B). Solvent A was a 0.1% formic acid solution made by adding 1 ml formic acid to 1000 ml water and then mixing and degassing the solution by ultra-sonication for 5 minutes. Solvent B was 80% acetonitrile (high-purity grade) in 0.1% formic acid solution that was made by mixing 800 ml acetonitrile, 1000 ml water and 1 ml formic acid, and degassing by ultra-sonication for 5 minutes. The column temperature was kept at ambient temperature and the temperature of the autosampler was 10° C. The mobile phase passed through the column at a rate of 0.3 milliliters per minute. The elution gradient for the HPLCS was performed as illustrated in Table 6. The injection volume was 10 µl of the prepared sample.

TABLE 6

Elution gradient of HPLCS.

| Time (min.) | Flow (ml/min.) | Solvent A (%) | Solvent B (%) | Curve |
|---|---|---|---|---|
| 0.00 | 0.3 | 100 | 0 | Linear 6 |
| 2.50 | 0.3 | 95 | 5 | linear 6 |
| 20.00 | 0.3 | 60 | 40 | linear 6 |
| 22.00 | 0.3 | 0 | 100 | linear 6 |
| 30.00 | 0.3 | 0 | 100 | linear 6 |
| 30.01 | 0.3 | 100 | 0 | linear 6 |
| 35.00 | 0.3 | 100 | 0 | linear 6 |

The mass-to-charge ratio of the eluting metabolites was determined using a mass spectrometry system including an electrospray ion source (ESI) and a quadruple ion detector scanning in the positive ion mode. The electrospray ionization voltage was set to about 3.0 to about 4.0 kV and the heated transfer capillary to 250° C. Nitrogen sheath and auxiliary gas settings were 70 and 5 units, respectively. For quantification of metabolites, the scan cycle consisted of a two full scan (1 s/scan) mass spectrum acquired over m/z 105-1000 in the positive ion mode. The max injection time was 300 ms, and the source ionization was about 5.0 kV. The apparatus was tuned on a mixture of butylated amino acids (e.g., Phe, Pro, Trp).

Two independent analyses of each of twenty-five AD subjects, thirty CTRL subjects, and twenty MCI subjects were performed. The independent analyses were referred to as "Run #1" and "Run #2." Before the biomolecular analyses were preformed, two separate aliquots were drawn from the original urine sample. One of these aliquots was designated for Run #1 and the other for Run #2. Subsequent sample processing, metabolite extraction, and analytical measurement were independent for each Run. The average time between Run #1 and Run #2 was approximately 1 month. In addition, each Run comprised two replicate measurements from the same aliquot. The time between duplicate measurements can vary from tens of minutes to hours.

Prior to statistical analysis, all spectral peaks were aligned and normalized in order to allow for quantitative comparison across all subject samples. Alignment was achieved using software to adjust for minor differences in spectral peaks arising from variation in analyte chromatographic retention times. Subsequent LC/MS spectral peak normalization was accomplished by determining a proper scaling factor for each LC/MS data set, typically through the use of internal standards.

After the steps of alignment and normalization, the data consisted of sample-specific files of spectral peaks which are identified only by their mass-to-charge ratio and retention time. After normalization, the intensities of these spectral peaks are directly comparable across all AD, CTRL, and MCI samples. The spectral data also were subjected to a number of pre-processing steps. For example, based on signal-to-noise criteria, the data were filtered to exclude peaks not satisfying a defined threshold intensity value. Further, peaks which resisted satisfactory alignment across data sets were also excluded from consideration.

In order to determine the minimal optimal subset of spectral peaks which best segregate AD and CTRL samples, an approach known as Recursive Feature Elimination was used. First, a "classification algorithm" was chosen which accepts as input N components (i.e., N spectral peaks), and returns (i) the success of segregating CTRL and AD samples (as measured by specificity and sensitivity) achieved by a linear combination of the N components, and (ii) a ranking of the N input components based on their contribution to the classification. Next, all spectral peaks observed in Run #1 (aligned, normalized, and pre-processed as discussed above) were allowed as input to the classification algorithm. With these components as inputs, the algorithm was then run to converge upon a linear combination of input spectral peaks used to classify CTRL and AD samples. Next, the ranking criterion ("weight") was recorded for each input spectral peak. The weights are the coefficients in the linear combination of input components as determined by the algorithm (the final weight is actually a mean weight, averaged over multiple Cross-Validation iterations; see discussion below). The success in classifying CTRL and AD samples for the data from Run #1 was then computed (i.e., specificity and sensitivity; this is the "Training Performance"). Next, the "Cross-Validation" performance of this combination of spectral peaks in classifying CTRL and AD samples for the data from Run #1 using the Cross-Validation method was computed. The success in classifying CTRL and AD samples for the data from Run #2 was then computed (i.e., specificity and sensitivity; this is the "Test Performance"). The spectral peak with the lowest weight was removed. These steps were repeated until only one spectral peak remained. The minimum number of peaks required to achieve the highest success (i.e., the highest specificity and sensitivity) in segregating CTRL and AD samples was then determined. These markers are a linear combination of peaks, the coefficients in the combination being the weights corresponding to each peak. These markers are said to have been "trained" on Run #1. The performance (specificity and sensitivity) of the markers is then tested on data from Run #2 (the "Test Performance").

The term "Recursive Feature Elimination" reflects the successive pruning of the list of spectral peaks by one. FIG. 1 shows the Training Performance as a function of number of markers for AD and CTRL samples as analyzed by the LC/MS plasma lipid platform of Run #1. The algorithm progresses from right to left in the figure, initially considering all available spectral peaks and subsequently recursively eliminating inputs until only one peak remains. The horizontal axis is logarithmic. It should be noted that the Training Performance results can lead to overly optimistic expectation for the generalizability of marker performance, which must be accounted for.

Two different and independent classification algorithms were applied to determine the markers. The first algorithm involves a state-of-the-art approach referred to as a "Linear Support Vector Machine." See V. N. Vapnik, *Statistical Learning Theory*, John Wiley & Sons, New York (1998). This method has its origins in handwriting and biometric pattern recognition. It is designed to select for final markers with low mutual correlation, a desirable trait to avoid redundancy and minimize the number of markers. The second such algorithm is termed a "Logistic Classifier." See J. A. Anderson, *Logisitic Discrimination in Hand Book Statistics*, P. R. Krishnaiah and L. N. Kanal, eds., Vol. 2, pp. 169-191, Amsterdam (1982).

Three different tests of performance were applied to determining the markers. First, "Training Performance" refers to the sensitivity and specificity of a combination of markers (composed of the highest weighted components at a given point in the iterative peak elimination process) when applied to the entire set of data from the AD samples and the CTRL samples. Because Training Performance is carried out on the sample set which is used to determine the markers and the weightings of the constituent components, this type of test is expected to provide very high performance because the marker has been tailored to work very well for the sample set at hand.

Figure 2:
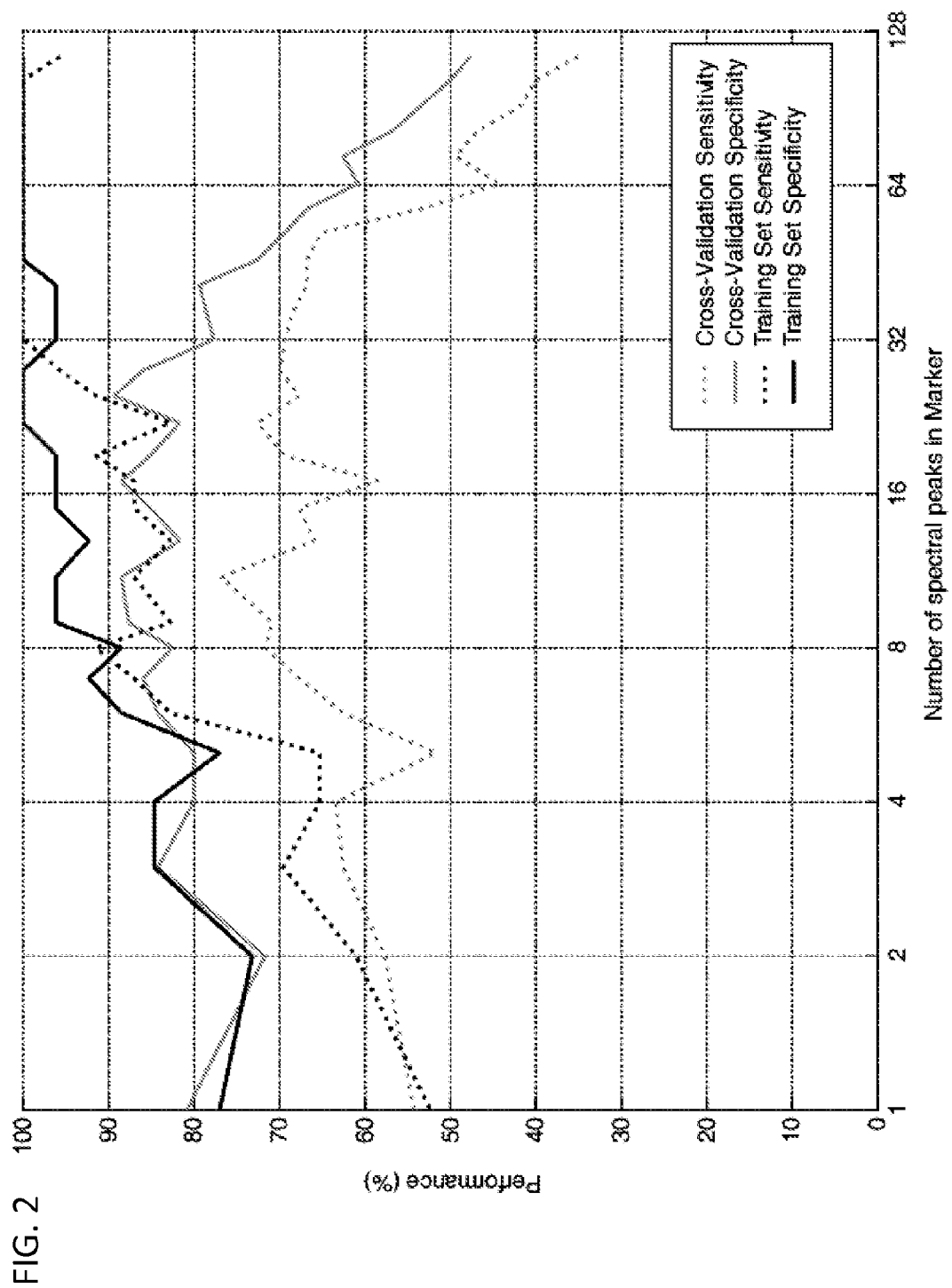
FIG. 2 shows an exemplary plot of "Cross-Validation Performance" and "Training Performance" on data sets as a function of the number of markers.

Second, "Cross-Validation Performance" is the sensitivity and specificity of markers which have been constructed based on a subset of the available samples and tested on the remaining samples which have been a priori intentionally left out. See T. Hastie et al., *The Elements of Statistical Learning*, Springer, New York (2001). From a complete set of samples, a test set of samples is extracted and temporarily left out of the analysis. For example, where there are twenty-five AD samples and thirty CTRL samples, the markers are constructed based only on twenty-one AD samples and twenty-six CTRL samples chosen at random. The performance (sensitivity and specificity) of the resultant markers are tested by classifying the remaining four AD and four CTRL samples that were excluded. The re-introduction of the test set allows for the calculation of sensitivity and specificity for the samples in the test set. This process is repeated many times, and each time a different, randomly chosen subset is left out. The number of iterations tested was of the order about 10 to about 100, and at the end of the exercise a mean and standard error was calculated and reported. The reported "Cross-Validation Performance" for the markers is the averaged performance of many such permutations. It is important to note that the purpose of Cross-Validation is to assess the generalizability of the markers, within the limitations posed by the availability of a relatively limited number of independent samples. As such, Cross-Validation Performance is calculated only using the data from either Run #1 or Run #2, but never both. The Cross-Validation Performance is an estimation of the performance of the markers on an independent test set of samples. Such an extrapolation is made possible by measuring the performance of the markers on the many permutations and combinations of subsets of the available samples; this process effectively simulates a situation in which many more samples are available. FIG. 2 shows the relation between Cross-Validation performance and Training Performance using the LC/MS plasma lipid platform. Note that the Cross-Validation performance is more conservative overall compared to the Training Performance. Cross-Validation performance is described in greater detail with respect to FIGS. 8 and 9.

Third, "Test Performance" is the sensitivity and specificity of markers which have been constructed using one sample set, and are being tested on a completely different and independent sample set. In many ways, this is the best possible type of performance test because it addresses directly the generalizability of the performance of the markers.

Upon determination of satisfactory markers from a number of spectral peaks, those peaks were submitted for biomolecular identification (e.g., by tandem mass spectrometry). If a spectral peak belonging to a marker is unidentifiable bioanalytically, the consequence of the exclusion of the unidentified spectral peak on performance is determined. If necessary, the process of determining the best performing markers may be re-initiated with such 'un-identifiable' peaks excluded from the initial set of spectral peaks available to the classification algorithm. This is an iterative procedure, concluding when markers of satisfactory performance have been identified, and all constituent spectral peaks of those markers have been biochemically identified. For given markers, in addition to those spectral peaks which characterize the markers, spectral peaks which are highly correlated to the ones constituting the markers are also submitted for identification, as these may serve as additional, alternate, or substitute peaks. Similarly, those spectral peaks which are characterized by high ranking weight coefficients, but initially not included as markers to achieve sufficient performance, are also submitted for identification and possible use as a marker and/or substitution for any un-identified marker peaks.

Table 7 below is a summary of the results for classifying AD and CTRL subjects utilizing 14 markers. A linear classifier was fitted based on the entire training set. This classifier was then applied to the test set. Point estimates of sensitivity and specificity based on the test set were calculated as the respective fractions of AD and control patients correctly classified. The Test Performance values (Test Sensitivity and Test Specificity columns of Table 7) are the sensitivity and specificity of markers developed on Run #1 and tested on Run #2 (i.e., no information from Run #2 has been used in defining these markers). "Cross-Validation" performance is as defined above, and is performed on samples from Run #1 (Cross-Validation Sensitivity and Cross-Validation Specificity columns of Table 7). Values in parentheses are standard errors ("SE") calculated based on the underlying binomial distribution of total numbers of AD and CTRL samples correctly classified. Cross-Validation performance is the mean of 150 'leave-8-out' iterations. Eight samples were randomly chosen (4 from each group) and set aside, and a classifier was constructed using the remaining samples. The 8 samples set aside comprised a test set, and the performance of the classifier thus produced was recorded. This procedure was repeated 150 times with different randomly chosen sets of 8 samples set aside. Based on the 150 classifiers produced in this procedure, a point estimate of test sensitivity was obtained by computing the average number of AD samples within the test sets which were correctly classified. Similarly, a point estimate of test specificity was calculated as the average number of CTRL samples within the test sets which were correctly classified. The standard errors of these estimates were approximated using the formula for the standard error of the corrected resampled t distribution.

TABLE 7

Summary of performance of fourteen markers.

| Platform | Test Sensitivity And SE (%) | Test Specificity and SE (%) | Cross-Validation Sensitivity and SE (%) | Cross-Validation Specificity and SE (%) |
|---|---|---|---|---|
| Urine LC/MS Polar | 82.61 (7.90) | 92.59 (5.04) | 83.17 (9.69) | 88.83 (6.74) |

Figure 3:
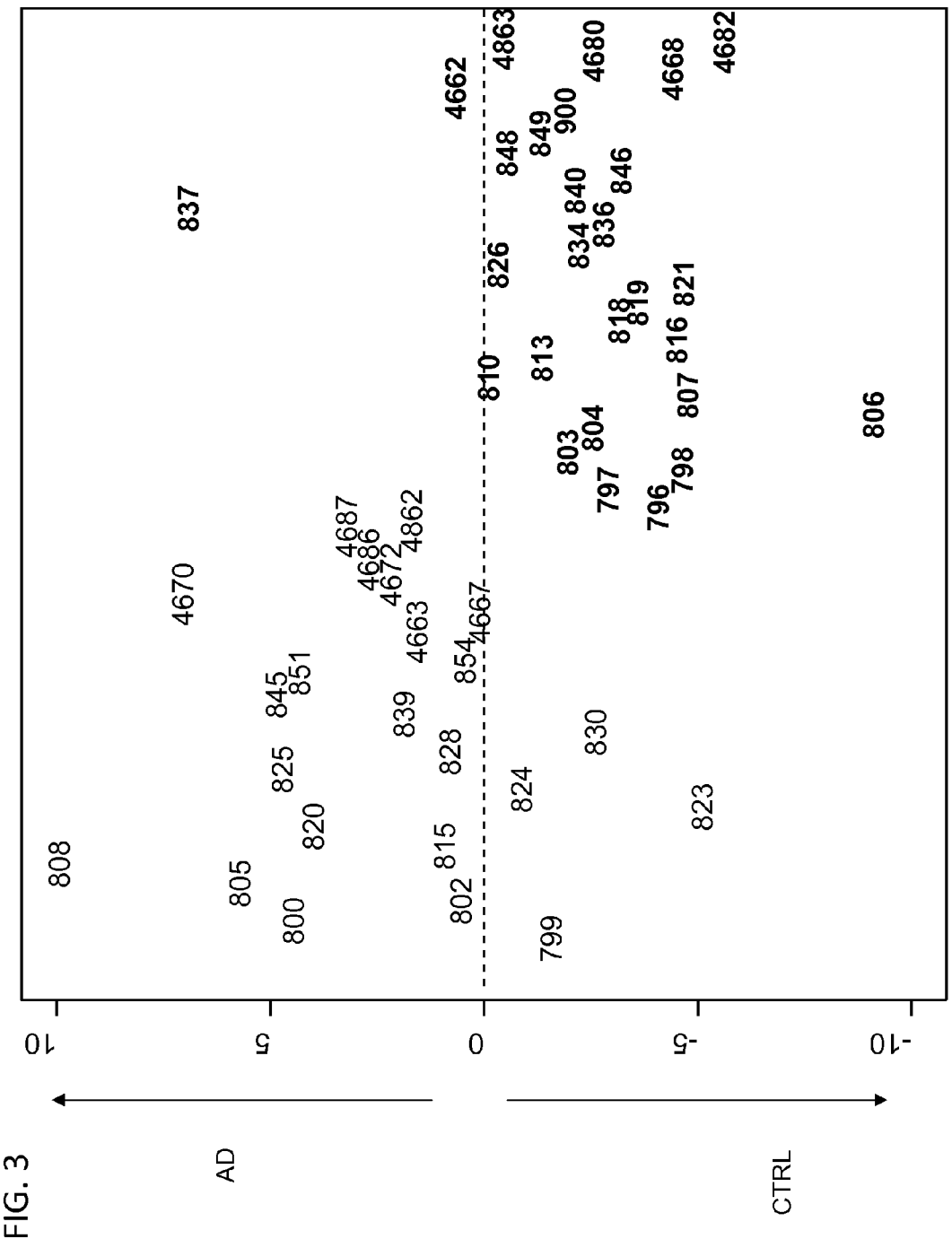
FIG. 3 shows an exemplary plot of Alzheimer's disease ("AD") and Normal ("CTRL") samples as classified by markers according to the present invention.

The Urine LC/MS Polar platform (i.e., an LC/MS analysis for profiling polar compounds in urine) yielded 14 markers, which demonstrated a sensitivity of 82.61% and a specificity of 92.59%. FIG. 3 shows a plot of all AD and CTRL samples analyzed in the present study by the LC/MS Polar urine metabolite platform. The vertical axis represents the distance from the decision boundary in arbitrary units for the 14-peak pattern of each sample. The dashed-line through zero represents the decision boundary as determined by the markers; samples which fall above the line are classified by the marker as AD, while samples below the line are classified as CTRL. The clinical diagnosis of each sample is indicated by the style of its data point. The bold annotated points represent subjects clinically diagnosed as CTRL, and the non-bold annotated points represent subjects clinically diagnosed as AD. These markers were constructed using exclusively Run #1 data, and the results shown here are the application of the resultant markers to Run #2 data. The horizontal axis is a sample index and contains no information.

The constituents of the LC/MS Polar urine markers are detailed in Table 3 below. The identities of three compounds have been identified with high confidence for the LC/MS Polar urine markers. Identification methods include Fourier-transform mass spectrometry to determine elemental composition and comparison of analyte mass and retention times to reference compounds. Table 8 shows the linear combination of the 14 markers, the coefficient of each marker in the linear combination represented quantitatively by the "Weight." The Weight represents the feature ranking of the markers. The weights are determined by a classification algorithm. The weights are the coefficients in the linear combination of input components as determined by the algorithm. The final weight is a mean weight, averaged over multiple Cross-Validation iterations. As stated above in reference to Table 3, each peak is designated by 'ABC.DEFG', where ABC is its mass-to-charge ratio ("MCR") and DE.FG minutes is the liquid chromatographic retention time ("LCRT"). For example, the first row of Table 8 shows an MCR of 169 and a LCRT of 3.42 minutes. The identified molecules have been verified using Fourier-transform mass spectrometry to calculate elemental composition from accurate mass measurements, as well as additional verification by evaluation with reference compounds.

TABLE 8

Fourteen Spectral Peaks from LC/MS Polar Urine Analysis.

| Row Number | Peak | Weight (arbitrary units) | Probable Identity |
|---|---|---|---|
| 1 | 169.0342 | 2.88 | |
| 2 | 246.1045 | 2.69 | |
| 3 | 120.1714 | 2.67 | Phenylalanine |
| 4 | 202.2205 | 2.35 | |
| 5 | 254.1066 | 2.31 | |
| 6 | 273.1798 | 2.20 | |
| 7 | 260.1944 | 2.18 | Glutamate |
| 8 | 153.0839 | 1.68 | |
| 9 | 203.1607 | 1.45 | |
| 10 | 245.1612 | 1.39 | |
| 11 | 218.1020 | 1.31 | Carnitine |
| 12 | 304.1929 | 1.27 | |
| 13 | 227.1050 | 0.59 | |
| 14 | 333.1633 | 0.54 | |

Candidates for the compounds represented by the remaining peaks have also been hypothesized. The accurate mass of the molecule characterized by the peak in row 1 is 169.036 amu. The matching elemental composition (in the Kyoto Encyclopedia of Genes and Genomes ("KEGG") & theoretical is $C_5H_5O_3N_4$. One possible candidate for the spectral peak is Urate, KEGG #366, because the compound was not butylated and therefore has no COOH group.

The accurate mass of the molecule characterized by the peak in row 2 is 246.181 amu. The matching elemental composition (KEGG & theoretical) is $C_{11}H_{24}N_3O_3$. One possible candidate for the spectral peak is L-homocitrulline, KEGG #2427. The compound was 1× butylated and thus has 1 COOH group.

The accurate mass of the molecule characterized by the peak in row 4 is 202.144 amu. The matching elemental composition (KEGG & theoretical) is $C_{10}H_{20}O_3N_1$. Possible candidates for the spectral peak include 4-methylene-glutamate, KEGG #651, 1 COOH group (1×-butylated); 4-acetamidobutanoate, KEGG #2946, 1 COOH group (1× butylated); 6-amino-2-oxohexanoate, KEGG #3239, 1 COOH group (1× butylated); (S)-5-amino-3-oxohexanoate, KEGG #3656, 1 COOH group (1×-butylated); L-2-aminoadipate 6-semialdehyde, KEGG #4076, 1 COOH group (1×-butylated); 2-amino-3-oxohexanoate, KEGG #5825, 1 COOH group (1×-butylated); N4 acetylaminobutanoate, KEGG #5937, 1 COOH group (1×-butylated); and 2-oxohex-trans-4-enoate, KEGG #6761, 1 COOH group (1× butylated, M+NH$_4$ ion).

The accurate mass of the molecule characterized by the peak in row 5 is 254.150 amu. The matching elemental composition (KEGG & theoretical) is $C_{12}H_{20}O_3N_3$. Possible candidates for the spectral peak include Nicotinurate (nicotinate and nicotinamide metabolism), KEGG #5380, 1 COOH group (1× butylated, M+NH$_4$ ion); and N-acetyl histidine, KEGG #2997, 1 COOH group (1×-butylated).

The accurate mass of the molecule characterized by the peak in row 6 is 273.181 amu. The matching elemental composition (KEGG & theoretical) is $C_{13}H_{25}O_4N_2$. One possible candidate for the spectral peak is N-Formimino-L-aspartate (histidine metabolism), KEGG #3409, 2 COOH groups (2×-butylated).

The accurate mass of the molecule characterized by the peak in row 9 is 203.110 amu. The matching elemental composition (theoretical) is $C_{10}H_{19}O_2S_1$.

The accurate mass of the molecule characterized by the peak in row 12 is 304.175 amu. The matching elemental composition (KEGG & theoretical) is $C_{14}H_{26}O_6N_1$. Possible candidates for the spectral peak include cis-aconitate, KEGG

417, 3 COOH groups (2× butylated, M+NH$_4$ ion) and trans-aconitate, KEGG #2341, 3 COOH groups (2× butylated, M+NH$_4$ ion).

The accurate mass of the molecule characterized by the peak in row 13 is 227.139 amu. The matching elemental composition (KEGG & theoretical) is $C_{11}H_{19}N_2O_3$. Possible candidates for the spectral peak include non-butylated tyrosine ethylester KEGG #1458, no COOH groups, 3-hydroxy-anthranilate (Tryptophan metabolism), KEGG #632, 1 COOH group (1× butylated, M+NH$_4$ ion); 3-hydroxy-2-methylpyridine-5-carboxylate (Vitamin B6 metabolism), KEGG #1270, 1 COOH group (1× butylated, M+NH$_4$ ion); 4-amino salicylate, KEGG #2518, 1 COOH group (1× butylated, M+NH$_4$ ion); and 1-carbapen-2-em-3-carboxylic acid, KEGG #6669, 1 COOH group (1× butylated, M+NH$_4$ ion).

The accurate mass of the molecule characterized by the peak in row 14 is 333.202 amu. The matching elemental composition (KEGG & theoretical) is $C_{15}H_{29}N_2O_6$. The possible candidates for the spectral peak include Saccharopine (Lysine metabolism), KEGG #449, 3 COOH groups (1× butylated) and 2-(hydroxymethyl)-3-(acetamidomethylene)succinate (Vitamin B6 metabolism), KEGG #4690, 2 COOH groups (2× butylated).

Figure 4:
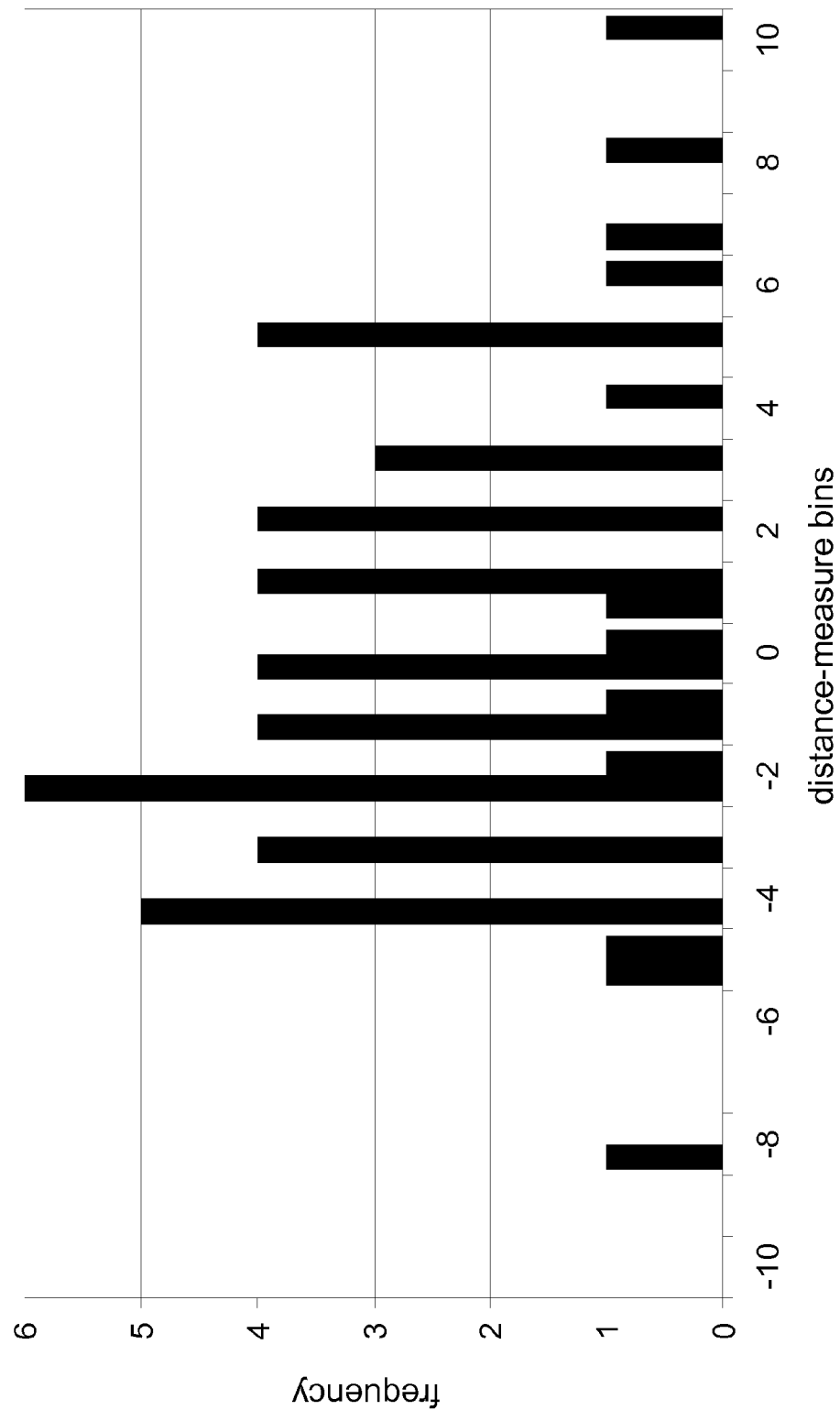
FIG. 4 shows a histogram of the "distance from the decision boundary" of the data presented in FIG. 3.

FIG. 4 shows a histogram of values of "distance from decision boundary" of FIG. 3 for samples classified as AD (black bars) and CTRL (gray bars). The metric "distance from decision boundary" represents the values which the combination of markers outputs to classify a sample. If that output value is positive, the sample is classified as AD (i.e., a "positive screen"); if the output value is negative, the sample is classified as CTRL (as in FIG. 3). This combination of markers has been constructed from the data of Run #1 of the LC/MS Polar urine metabolite platform and used to classify the samples from the independent Run #2 of the LC/MS Polar urine metabolite platform. The two distributions of AD and CTRL classifications are evident and are characterized by a univariate homoscedastic t-test p-value of $p=2\times10^{-6}$.

Figure 5:
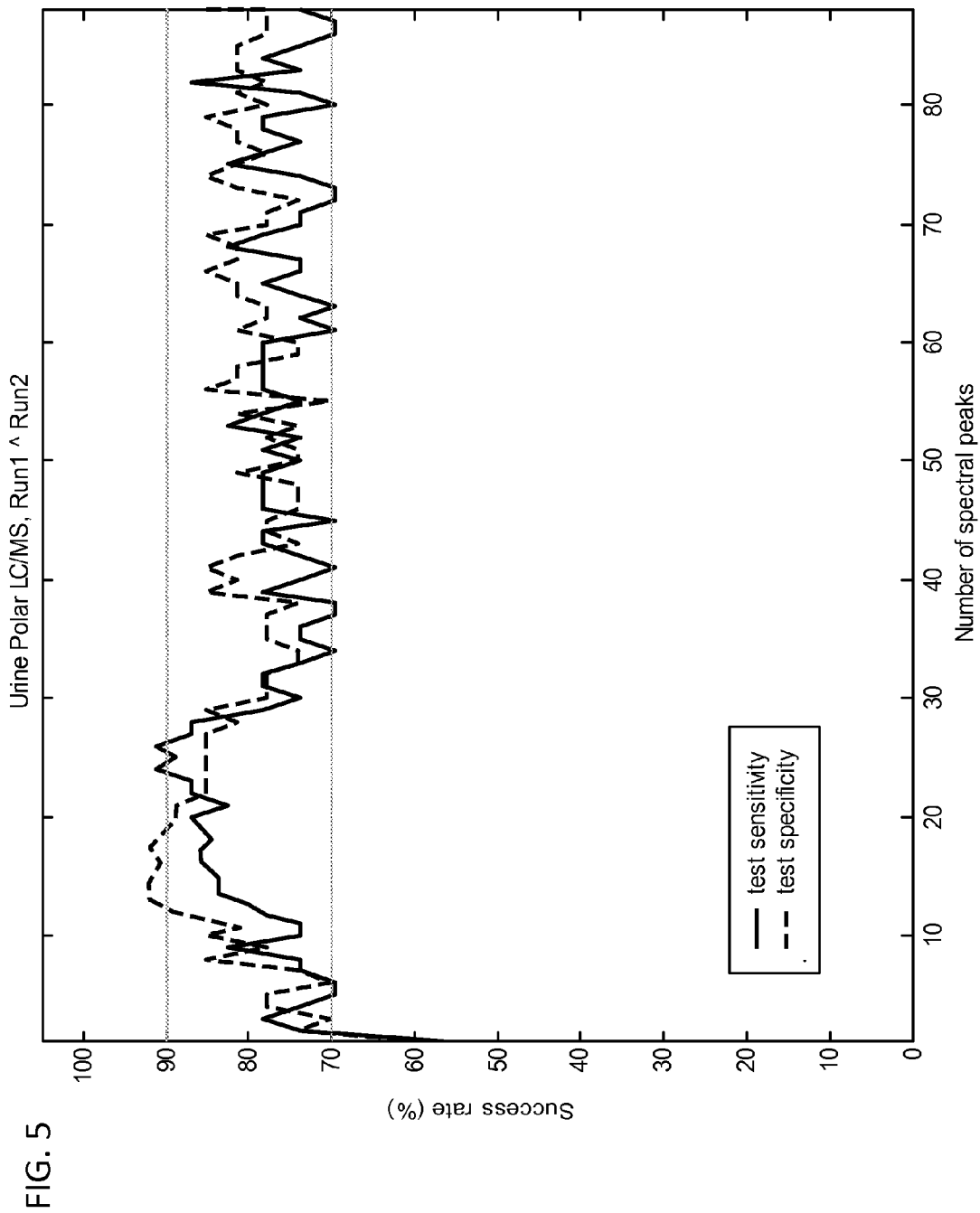
FIG. 5 shows an exemplary plot of "Test Performance" of sensitivity and specificity of a function of the number of markers from a urine LC/MS Polar metabolite platform.

FIG. 5 shows a plot of the Urine LC/MS Polar metabolite platform "Test Performance" of sensitivity and specificity as a function of number of markers, for AD and CTRL samples. The markers are constructed using Run #1 and tested on Run #2. Note that the standard error at 14 peaks (or markers) is 7.90% for sensitivity and 5.04% for specificity; these standard errors are calculated based on the underlying binomial distribution of correctly classified AD and CTRL samples.

Figure 6:
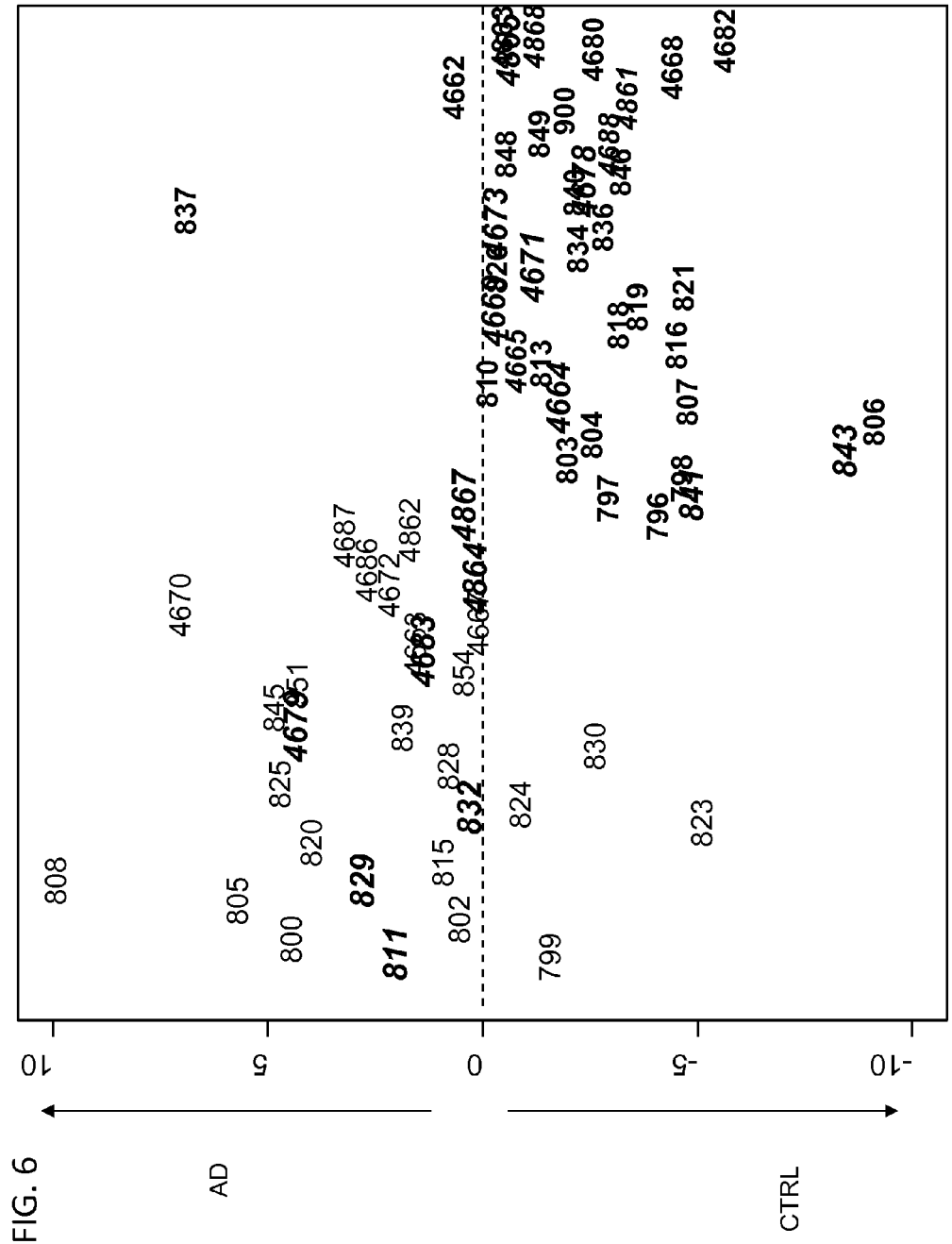
FIG. 6 shows an exemplary plot of all AD, CTRL and Mild Cognitive Impairment (MCI) samples as classified by markers according to the present invention.

In addition to classification of AD and CTRL subjects, the fourteen LC/MS Polar urine metabolite markers have also been applied to classify MCI subjects. The results are shown in FIG. 6, which also reproduces the results of the AD and CTRL subjects from FIG. 3. The MCI subjects are annotated in the plot by their dark sample identifier codes. The vertical axis represents distance from the decision boundary in arbitrary units. The horizontal axis is arbitrary and is included for clarity. It is seen that many of the MCI subjects are classified very near the decision boundary and that roughly half of the MCI subjects are classified in the AD range and half in the CTRL range.

Figure 7:
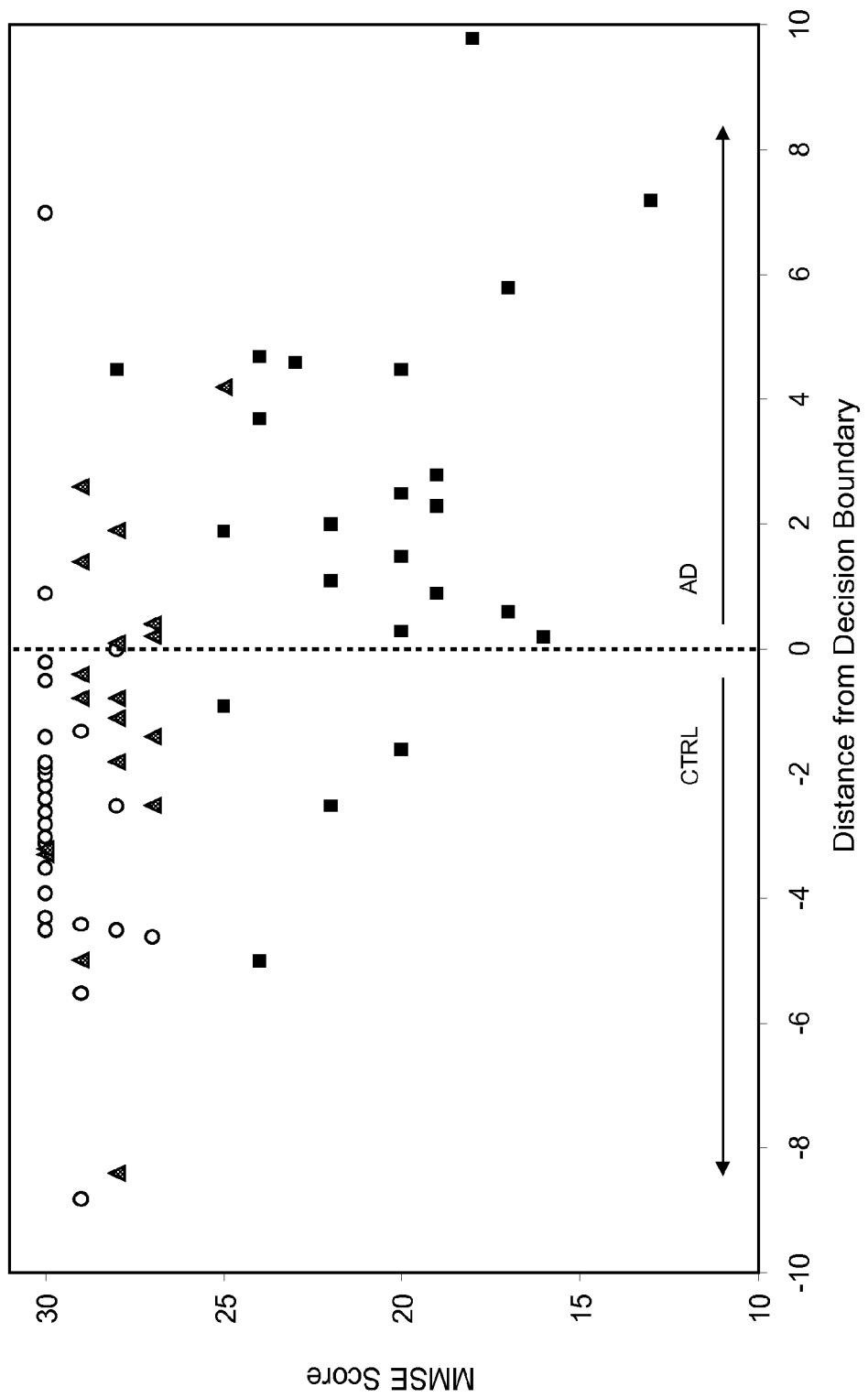
FIG. 7 is an exemplary plot of the Mini-Mental State Examination score as a function of "distance from the decision boundary" for AD, CTRL, and MCI samples.

FIG. 7 shows a plot of the reported Mini-Mental State Examination (MMSE) score as a function of the distance from the decision boundary as determined by the 14-component urine marker of Table 3 for AD (■), CTRL (O), and MCI (▲) samples, for the 14 markers derived from the LC/MS Polar urine metabolite platform. Recall that a positive distance measure indicates the marker classification is AD (a positive screen), while a negative distance measure is a classification by the marker of CTRL.

Figure 8:
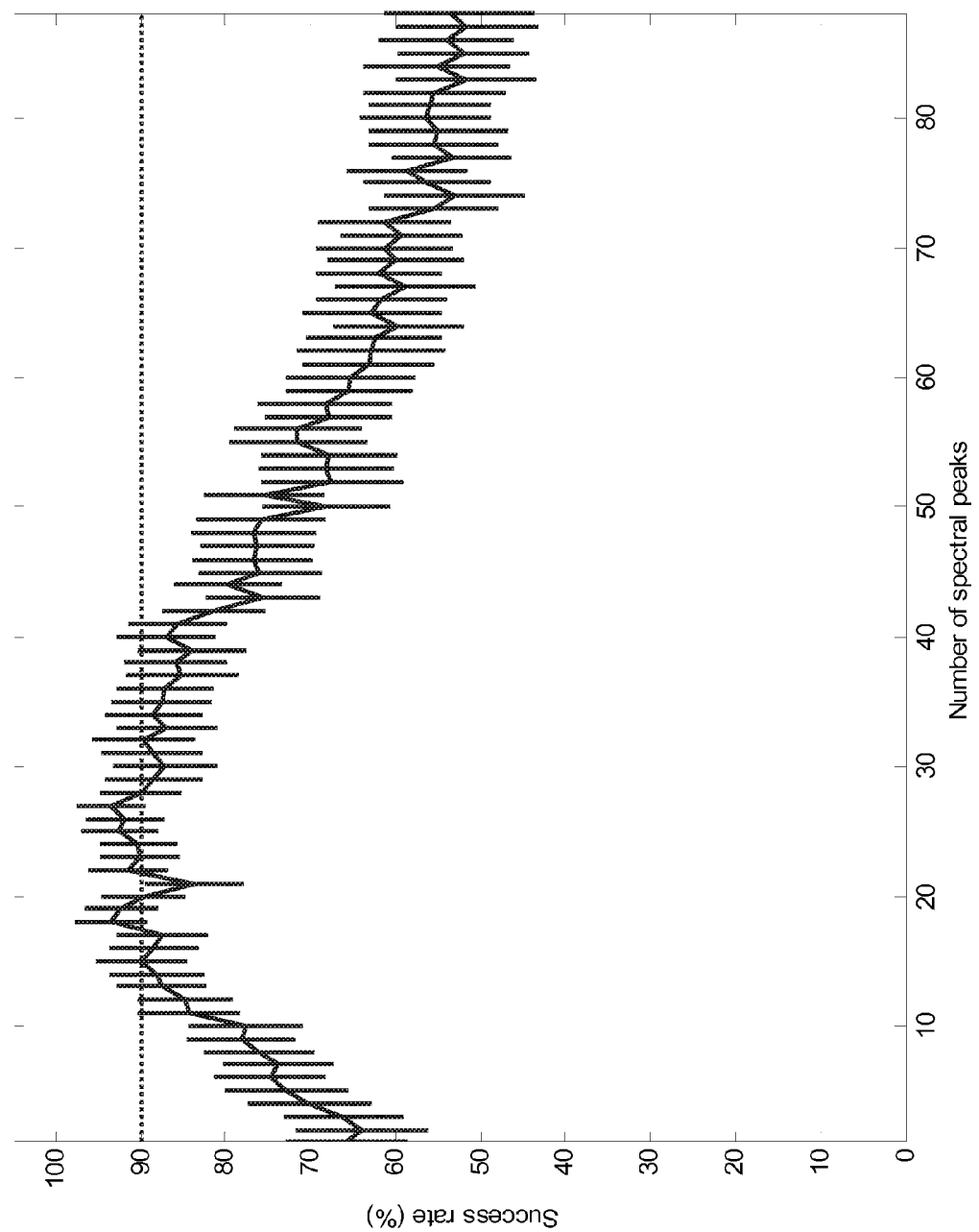
FIG. 8 shows an exemplary plot of cross-validated estimates of specificity.

Cross validation was discussed above in relation to FIG. 2. FIG. 8 shows cross-validated estimates of sensitivity for the Urine LC/MS Polar metabolite platform with standard error bars superimposed. Starting with 88 urine LC/MS spectral peaks, at each value of "Number of spectral peaks" the following procedure was performed 150 times. Eight samples were randomly chosen (4 AD+4 CTRL) and set aside, and a classifier was constructed using the remaining samples. The eight samples set aside comprised a test set. Based on the 150 classifiers thus produced, a point estimate of test sensitivity was obtained by computing the average number of AD samples within the test sets that were correctly classified. The standard error of this estimate was approximated using the formula for the standard error of the corrected resampled t. In addition, a ranking of all the peaks at a given number of spectral peaks was obtained by averaging the weights given by the 150 classifiers to each spectral peak and sorting the peaks in descending order of the absolute values of these mean weights. The transition to the next lower dimension was made by eliminating the peak with the lowest absolute mean weight. The plot shows the estimated test sensitivity on which intervals of one standard error (positive and negative) are superimposed.

Figure 9:
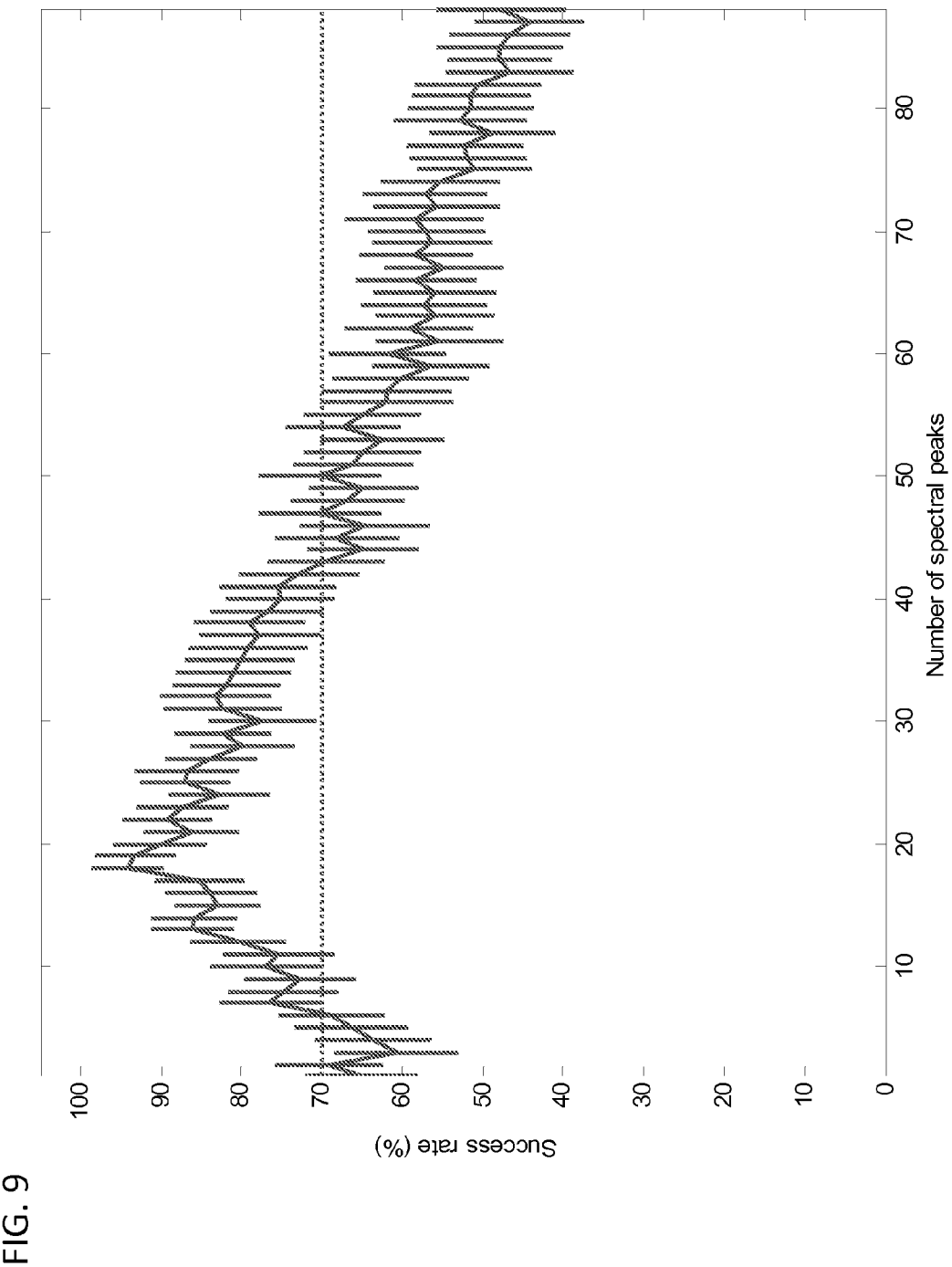
FIG. 9 shows an exemplary plot of cross-validated estimates of sensitivity.

FIG. 9 shows cross-validated estimates of specificity for the Urine LC/MS Polar metabolite platform with standard error bars superimposed. Starting with 88 urine LC/MS spectral peaks, at each value of "Number of spectral peaks" the following procedure was performed 150 times. Eight samples were randomly chosen (4 AD+4 CTRL) and set aside, and a classifier was constructed using the remaining samples. The eight samples set aside comprised a test set. Based on the 150 classifiers thus produced, a point estimate of test sensitivity was obtained by computing the average number of AD samples within the test sets that were correctly classified. The standard error of this estimate was approximated using the formula for the standard error of the corrected resampled t. In addition, a ranking of all the peaks at a given number of spectral peaks was obtained by averaging the weights given by the 150 classifiers to each spectral peak and sorting the peaks in descending order of the absolute values of these meanweights. The transition to the next lower dimension was made by eliminating the peak with the lowest absolute mean weight. The plot shows the estimated test sensitivity on which intervals of one standard error (positive and negative) are superimposed.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

Throughout the description, where compositions are described as having, including, or comprising specific components, or where processes are described as having, including, or comprising specific process steps, it is contemplated that compositions of the present invention also consist essentially of, or consist of, the recited processing components, and that the processes of the present invention also consist essentially of, or consist of, the recited processing steps.

It should be understood that the order of steps or order for performing certain actions is immaterial so long as the invention remains operable. Moreover, two or more steps or actions may be conducted simultaneously.

INCORPORATION BY REFERENCE

The entire disclosure of each of the aforementioned patent and scientific documents is expressly incorporated by reference herein for all purposes.

What is claimed is:

1. A method for screening an individual for being at risk of having or developing Alzheimer's disease, the method comprising the steps of:
   detecting the amount of at least two markers in a sample from a patient; and
   comparing the detected amount of each of the at least two markers with an amount of each of the at least two markers from a standard, wherein a difference in the amount of each of the at least two markers between the sample and the standard indicates a positive screen,
   wherein the markers are selected from the group consisting of: urate, L-homocitrulline, and phenylalanine.

2. The method of claim 1, wherein the amount of each of the at least two markers is detected using one or more analytical techniques selected from the group consisting of an immunoassay, mass spectroscopy, chromatography, chemical analysis, a colorimetric assay, spectrophotometric analysis, electrochemical analysis, and nuclear magnetic resonance.

3. The method of claim 1, wherein the sample comprises a body fluid.

4. The method of claim 3, wherein the body fluid is selected from the group consisting of whole blood, blood plasma, blood serum, cerebrospinal fluid, saliva, urine, seminal fluid, breast nipple aspirate, pancreatic fluid, and combinations thereof.

5. The method of claim 4, wherein the body fluid comprises urine.

6. The method of claim 1, wherein the standard is obtained from at least one healthy person, the at least one healthy person having a predetermined dietary intake for a predetermined time before sampling.

7. The method of claim 6, wherein the sample is obtained from a patient of the same sex as the at least one healthy person, the patient having the same predetermined dietary intake for the same predetermined time before sampling as the at least one healthy person.

8. A method for screening an individual for being at risk of having or developing Alzheimer's disease, the method comprising the step of:
   comparing, using a suitably programmed computer, an amount of each of at least two markers in a sample from a patient with an amount of each of the at least two markers from a standard, wherein a difference in the amount of a statistically significant number of the at least two markers between the sample and the standard indicates a positive screen and wherein the markers are selected from the group consisting of: urate, L-homocitrulline, and phenylalanine.

9. The method of claim 8, wherein the screen is characterized by a specificity of at least about 50%.

10. The method of claim 8, wherein the screen is characterized by a sensitivity of at least about 50%.

11. The method of claim 8, wherein the amount of each of the at least two markers is detected using one or more analytical techniques selected from the group consisting of an immunoassay, mass spectroscopy, chromatography, chemical analysis, a colorimetric assay, spectrophotometric analysis, electrochemical analysis, and nuclear magnetic resonance.

12. The method of claim 8 wherein the sample comprises a body fluid.

13. The method of claim 12, wherein the body fluid is selected from the group consisting of whole blood, blood plasma, blood serum, cerebrospinal fluid, saliva, urine, seminal fluid, breast nipple aspirate, pancreatic fluid, and combinations thereof.

14. The method of claim 13, wherein the body fluid comprises urine.

15. The method of claim 8, wherein the standard is obtained from at least one healthy person, the at least one healthy person having a predetermined dietary intake for a predetermined time before sampling.

16. The method of claim 15, wherein the sample is obtained from a patient of the same sex as the at least one healthy person, the patient having the same predetermined dietary intake for the same predetermined time before sampling as the at least one healthy person.

17. The method of claim 8, wherein the screen is characterized by a specificity of at least about 60%.

18. The method of claim 8, wherein the screen is characterized by a specificity of at least about 70%.

19. The method of claim 8, wherein the screen is characterized by a specificity of at least about 80%.

20. The method of claim 8, wherein the screen is characterized by a specificity of at least about 90%.

21. The method of claim 8, wherein the screen is characterized by a sensitivity of at least about 60%.

22. The method of claim 8, wherein the screen is characterized by a sensitivity of at least about 70%.

23. The method of claim 8, wherein the screen is characterized by a sensitivity of at least about 80%.

24. The method of claim 8, wherein the screen is characterized by a sensitivity of at least about 90%.

25. The method of claim 1, wherein the amount of at least three markers are detected in a sample from a patient, and wherein the markers comprise urate, L-homocitrulline, and phenylalanine.

26. The method of claim 8, wherein the amount of at least three markers are detected in a sample from a patient, and wherein the markers comprise urate, L-homocitrulline, and phenylalanine.

27. The method of claim 1, wherein the at least two markers comprise urate and L-homocitrulline.

28. The method of claim 1, wherein the at least two markers comprise urate and phenylalanine.

29. The method of claim 1, wherein the at least two markers comprise L-homocitrulline and phenylalanine.

30. The method of claim 8, wherein the at least two markers comprise urate and L-homocitrulline.

31. The method of claim 8, wherein the at least two markers comprise urate and phenylalanine.

32. The method of claim 8, wherein the at least two markers comprise L-homocitrulline and phenylalanine.

* * * * *